United States Patent
Gewirtz

(10) Patent No.: US 7,851,452 B2
(45) Date of Patent: Dec. 14, 2010

(54) METHODS OF USE OF BCL-6-DERIVED NUCLEOTIDES TO INDUCE APOPTOSIS

(75) Inventor: Alan M. Gewirtz, Penn Valley, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 421 days.

(21) Appl. No.: 10/593,578

(22) PCT Filed: Mar. 22, 2005

(86) PCT No.: PCT/US2005/009349

§ 371 (c)(1),
(2), (4) Date: Jun. 4, 2007

(87) PCT Pub. No.: WO2005/092030

PCT Pub. Date: Oct. 6, 2005

(65) Prior Publication Data

US 2008/0153765 A1 Jun. 26, 2008

Related U.S. Application Data

(60) Provisional application No. 60/555,207, filed on Mar. 22, 2004.

(51) Int. Cl.
*A61K 31/70* (2006.01)
*C07H 21/02* (2006.01)
*C07H 21/04* (2006.01)
*C12Q 1/68* (2006.01)

(52) U.S. Cl. .................. 514/44 A; 435/6; 435/375; 435/377; 435/320.1; 536/23.1; 536/24.1; 536/24.5

(58) Field of Classification Search ........................ None
See application file for complete search history.

(56) References Cited

U.S. PATENT DOCUMENTS

| | | | | |
|---|---|---|---|---|
| 5,624,803 | A | * | 4/1997 | Noonberg et al. ............. 435/6 |
| 6,140,125 | A | * | 10/2000 | Taylor et al. ................ 435/375 |
| 6,506,559 | B1 | | 1/2003 | Fire et al. |
| 2002/0114784 | A1 | * | 8/2002 | Li et al. ..................... 424/93.2 |
| 2004/0259247 | A1 | * | 12/2004 | Tuschl et al. ................ 435/375 |

OTHER PUBLICATIONS

Opalinska et al., Blood vol. 102(11):137A-138A, 2003.*
Artiga MJ et al. "A short mutational hot spot in the first intron of BCL-6 is associated with increased BCL-6 expression and with longer overall survival in large B-cell lymphomas," Am J Pathol. Apr. 2002; 160(4): 1371-80.
Baron BW et al. "Identification of the gene associated with the recurring chromosomal translocations t(3;14)(q27;g32) and t(3:22)(g27;q11) in B-cell lymphomas," Proc Natl Acad Sci U S A Jun. 1, 1993;90(11):5262-6.
Barrans SL et al. "Rearrangement of the BCL6 locus at 3q27 is an independent poor prognostic factor in nodal diffuse large B-cell lymphoma." Br J Haematol May 2002,117(2):322-32.

Braaten KM et al. "BCL-6 expression predicts improved survival in patients with primary central nervous system lymphoma." Clin Cancer Res. Mar. 2003;9(3):1063-9.
Brindle KM, Br. J. Radiol. 76 Spec., No. 2:S111-7, 2003.
Buchwald et al., Surgery 88:507, 1980.
Caudy AA et al., Gene & Devel, 16:2491-96.
Chang CC et al, "BCL-6, a POZ/zinc-finger protein, is a sequence-specific transcriptional repressor" PNAS 93(14): 6947-52, 1996.
Chang CC et al. "Expression of p53, c-Myc, or Bcl-6 suggests a poor prognosis in primary central nervous system diffuse large B-cell lymphoma among immunocompetent individuals." Arch Pathol Lab Med. Feb. 2003;127(2):208-12.
Goodson, Medical Applications of Controlled Release, Supra, vol. 2, pp. 115-138, 1984.
Gifford et al., "Identification of antisense nucleic acid hybridization sites in mRNA molecules with self-quenching, fluorescent reporter molecules", Nucleic Acids Research; 2005, vol. 33, No. 3, 9 Pages.
Harris NL et al. "A revised European-American classification of lymphoid neoplasms: a proposal from the International Lymphoma Study Group," Blood. Sep. 1, 1994;84(5):1361-92.
Jerkeman M et al. "Prognostic implications of BCL6 rearrangement in uniformly treated patients with diffuse large B-cell lymphoma—a Nordic Lymphoma Group study." Int J Oncol. Jan. 2002;20(1):161-5.
Kawasaki C et al. "Rearrangements of bcl-1, bcl-2, bcl-6, and c-myc in diffuse large B-cell lymphomas." Leuk Lymphoma. Sep.-Oct. 2001;42(5):1099-106.
Lossos IS et al. "Expression of a single gene, BCL-6, strongly predicts survival in patients with diffuse large B-cell lymphoma." Blood. Aug. 15, 2001;98(4):945-51.
Lahorte CM et al., Eur. J. Nucl. Med. Mol. Imaging 31(6)887-919, 2004.
Langer, Science, 249:1527-1533, 1990.
Kalota A, "Design of antisense oligonucleotides and short interfering RNA duplexes (siRNA) targeted to BCL6 mRNA: towards rational drug development for specific lymphoma subsets". JB. Blood Cells Mol Dis. May-Jun. 2007;38(3):199-203. Epub Jan. 24, 2007.
Opalinska et al., "Oxetance modified, Conformationaliy Constrained, antisense Oligodeoxyribounucleotides function efficiently as gene silencing molecules", Nucleic Acids Research, 2004, vol. 32. No. 19, 5791-5799.

(Continued)

*Primary Examiner*—Sean R McGarry
(74) *Attorney, Agent, or Firm*—Pearl Cohen Zedek Latzer, LLP; Mark S. Cohen

(57) ABSTRACT

This invention provides methods of inducing apoptosis in a bcl-6-expressing cell and methods of treating a subject with a cancer comprising a bcl-6-expressing cell, comprising administration of a composition that reduces the amount of the bcl-6 protein or of an mRNA molecule encoding same, a composition comprising a nucleic acid molecule complementary to or corresponding to a region of the mRNA molecule, or a vector expressing the nucleic acid molecule. In another embodiment, the present invention provides an isolated nucleic acid molecule having a sequence corresponding to or complementary to accessible regions of bcl-6 mRNA, and vectors, cells, compositions, and kits comprising same.

49 Claims, 10 Drawing Sheets

OTHER PUBLICATIONS

Sánchez-Beato M et al. "Cell cycle dereoulation in B-cell lymphomas." Blood. Feb. 15, 2003;101(4)1220-35. Epub Sep. 12, 2002.

Saudek et al., N. Engl. J. Med. 321:574.1989.

Sefton, CRC Crit. Ref. Biomed. Eng. 14:201, 1987.

Shaffer AL et al. "BCL-6 represses genes that function in lymphocyte differentiation, inflammation, and cell cycle control." Immunity. Aug. 13, 2000(2)199-212.

Sokol et al., "Real time detection of DNA-RNA hybridization in Living Cells", Proc. Natl. Acad. Sci. USA, vol. 95, pp. 11538-11543, Sep. 1998.

Tang TT et al. "The forkhead transcription factor AFX activates apoptosis by induction of the BCL-6 transcriptional repressor." J Biol Chem. Apr. 19, 2002;277(16)14255-65. Epub Jan. 2, 2002.

Ueda C et al. "Non-immunoglobulin/BCL6 gene fusion in diffuse large B-cell lymphoma: prognostic implications." Leuk Lymphoma. Jul. 2002;43(7):1375-81.

Vitolo U et al. "Point mutations of the BCL-6 gene: clinical and prognostic correlation in B-diffuse large cell lymphoma." Leukemia. Feb. 2002;16(2):268-75.

Ye BH et al. "Chromosomal translocations cause deregulated BCL6 expression by promoter substitution in B-cell lymphoma." EMBO J. Dec. 15, 1995;14(24):6209-17.

Ye BH et al, "The BCL-6 proto-oncogene controls germinal-centre formation and Th2-type inflammation." Nat Genet. Jun. 1997;16(2)161-70.

International Search Report of Application No. PCT/US05/09349 dated Aug. 16, 2006.

* cited by examiner

Figure 3
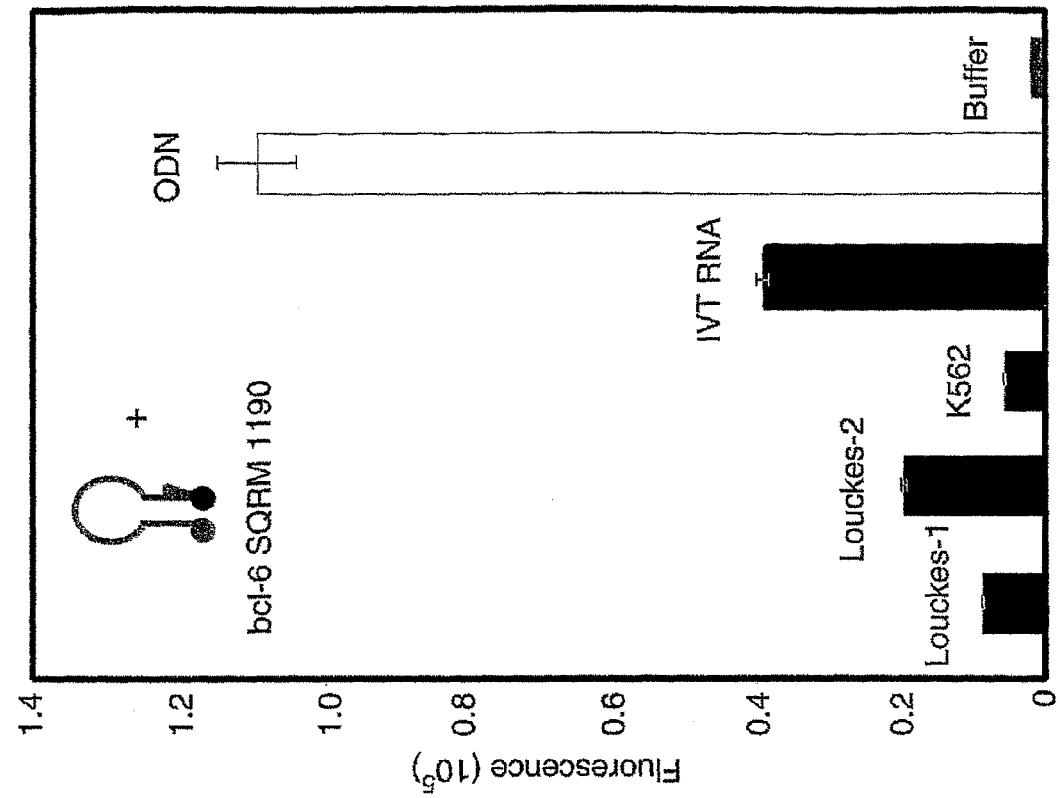
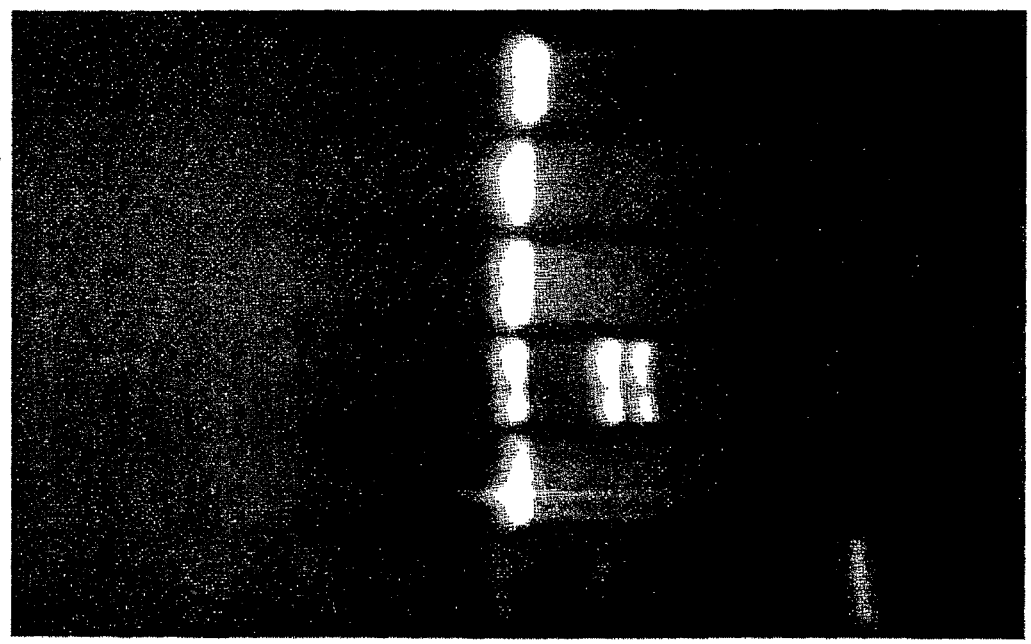

… (US 7,851,452 B2)

METHODS OF USE OF BCL-6-DERIVED NUCLEOTIDES TO INDUCE APOPTOSIS

CROSS REFERENCE TO RELATED APPLICATION

This application claims priority of U.S. Provisional Application Ser. No. 60/555,207, filed Mar. 22, 2004, which is hereby incorporated in its entirety by reference herein.

STATEMENT REGARDING FEDERALLY SPONSORED RESEARCH OR DEVELOPMENT

The invention described herein was supported in part by a grant from The National Institutes of Health (Grant No. PO1-CA72765). The U.S. Government may have certain rights in this invention.

FIELD OF INVENTION

This invention provides methods of inducing apoptosis in a bcl-6-expressing cell and methods of treating a subject with a cancer comprising a bcl-6-expressing cell, comprising administration of a composition that reduces the amount of the bcl-6 protein or of an mRNA molecule encoding same, a composition comprising a nucleic acid molecule complementary to or corresponding to a region of the mRNA molecule, or a vector expressing the nucleic acid molecule. In another embodiment, the present invention provides an isolated nucleic acid molecule having a sequence corresponding to or complementary to accessible regions of bcl-6 mRNA, and vectors, cells, compositions, and kits comprising same.

BACKGROUND OF THE INVENTION

BCL-6 is a zing finger protein that acts as a sequence-specific transcriptional repressor, binding to DNA with its amino-terminal Pox virus zinc finger (POZ) domain. Bcl-6 is frequently deregulated in non-Hodgkin lymphomas. The altered expression of Bcl-6 arises mostly from 3q27 translocations, in which the 5' non-coding region is replaced by a heterologous promoter, leading to over-expression of the protein.

The term "lymphoma" encompasses more than 40 related types of cancer that develop from lymphocytes (cells of the immune system). Lymphoma arises when one of these cells undergoes a transformation into a malignant cell and begins to grow abnormally, dividing and forming tumors. Lymphomas are divided into two general types: Hodgkin's disease and non-Hodgkin's lymphomas.

SUMMARY OF THE INVENTION

This invention provides methods of inducing apoptosis in a bcl-6-expressing cell and methods of treating a subject with a cancer comprising a bcl-6-expressing cell, comprising administration of a composition that reduces the amount of the bcl-6 protein or of an mRNA molecule encoding same, a composition comprising a nucleic acid molecule complementary to or corresponding to a region of the mRNA molecule, or a vector expressing the nucleic acid molecule. In another embodiment, the present invention provides an isolated nucleic acid molecule having a sequence corresponding to or complementary to accessible regions of bcl-6 mRNA, and vectors, cells, compositions, and kits comprising same.

In one embodiment, the present invention provides a method of inducing apoptosis in a bcl-6-expressing cell, comprising contacting the bcl-6-expressing cell with a composition that reduces an amount of the bcl-6 protein or of a ribonucleic acid (RNA) molecule encoding the bcl-6 protein, thereby inducing apoptosis in a bcl-6-expressing cell.

In another embodiment, the present invention provides a method of inducing apoptosis in a bcl-6-expressing cell, comprising contacting the bcl-6-expressing cell with a composition comprising a nucleic acid molecule complementary to a region of a RNA molecule encoding the bcl-6 protein, thereby inducing apoptosis in a bcl-6-expressing cell.

In another embodiment, the present invention provides a method of inducing apoptosis in a bcl-6-expressing cell, comprising contacting the bcl-6-expressing cell with a composition comprising a nucleic acid molecule corresponding to a region of a RNA molecule encoding the bcl-6 protein, thereby inducing apoptosis in a bcl-6-expressing cell.

In another embodiment, the present invention provides a method of inducing apoptosis in a bcl-6-expressing cell, comprising contacting the bcl-6-expressing cell with a vector expressing a nucleic acid molecule complementary to a region of a RNA molecule encoding the bcl-6 protein, thereby inducing apoptosis in a bcl-6-expressing cell.

In another embodiment, the present invention provides a method of inducing apoptosis in a bcl-6-expressing cell, comprising contacting the bcl-6-expressing cell with a vector expressing a nucleic acid molecule corresponding to a region of a RNA molecule encoding the bcl-6 protein, thereby inducing apoptosis in a bcl-6-expressing cell.

In another embodiment, the present invention provides a method of treating a subject with a cancer comprising a bcl-6-expressing cell, comprising contacting the subject with a composition that reduces an amount of the bcl-6 protein or of a RNA molecule encoding the bcl-6 protein, thereby treating a subject with cancer comprising a bcl-6-expressing cell.

In another embodiment, the present invention provides a method of treating a subject with a cancer comprising a bcl-6-expressing cell, comprising contacting the subject with a composition comprising a nucleic acid molecule complementary to a region of a RNA molecule encoding the bcl-6 protein, thereby treating a subject with cancer comprising a bcl-6-expressing cell.

In another embodiment, the present invention provides a method of treating a subject with a cancer comprising a bcl-6-expressing cell, comprising contacting the subject with a composition comprising a nucleic acid molecule corresponding to a region of a RNA molecule encoding the bcl-6 protein, thereby treating a subject with cancer comprising a bcl-6-expressing cell.

In another embodiment, the present invention provides a method of treating a subject with a cancer comprising a bcl-6-expressing cell, comprising contacting the subject with a vector expressing a nucleic acid molecule complementary to a region of a RNA molecule encoding the bcl-6 protein, thereby treating a subject with cancer comprising a bcl-6-expressing cell.

In another embodiment, the present invention provides a method of treating a subject with a cancer comprising a bcl-6-expressing cell, comprising contacting the subject with a vector expressing a nucleic acid molecule corresponding to a region of a RNA molecule encoding the bcl-6 protein, thereby treating a subject with cancer comprising a bcl-6-expressing cell.

In another embodiment, the present invention provides an isolated nucleic acid molecule having a sequence selected from the sequences set forth in SEQ ID No: 1-10. In another embodiment, the present invention provides an isolated nucleic acid molecule having a sequence complementary to a sequence selected from the sequences set forth in SEQ ID No: 1-10.

BRIEF DESCRIPTION OF THE FIGURES

FIG. 3. A. Use of in vitro RNaseH cleaving assay to confirm hybridization of SQRM 1190-1222 with the bcl-6 transcript. Bcl-6 mRNA was incubated with RNaseH and SQRM 831 (lane 2), RNaseH and 1190-1222 (lane 3), RNaseH and 1367 (lane 4), nothing (lane 5), or RNaseH alone (lane 6). B. bcl-6 SQRM1190-1222 was incubated with various targets and the fluorescence signal was measured. Louckes-1 (20 mg), Louckes-2 (40 mg) and K562 are RNA samples isolated from cell extracts. SQRM was also incubated with in vitro transcribed RNA (IVT RNA; a positive control for SQRM/RNA hybridization) and an ODN (positive control for SQRM function).

DETAILED DESCRIPTION OF THE INVENTION

Figure 1:
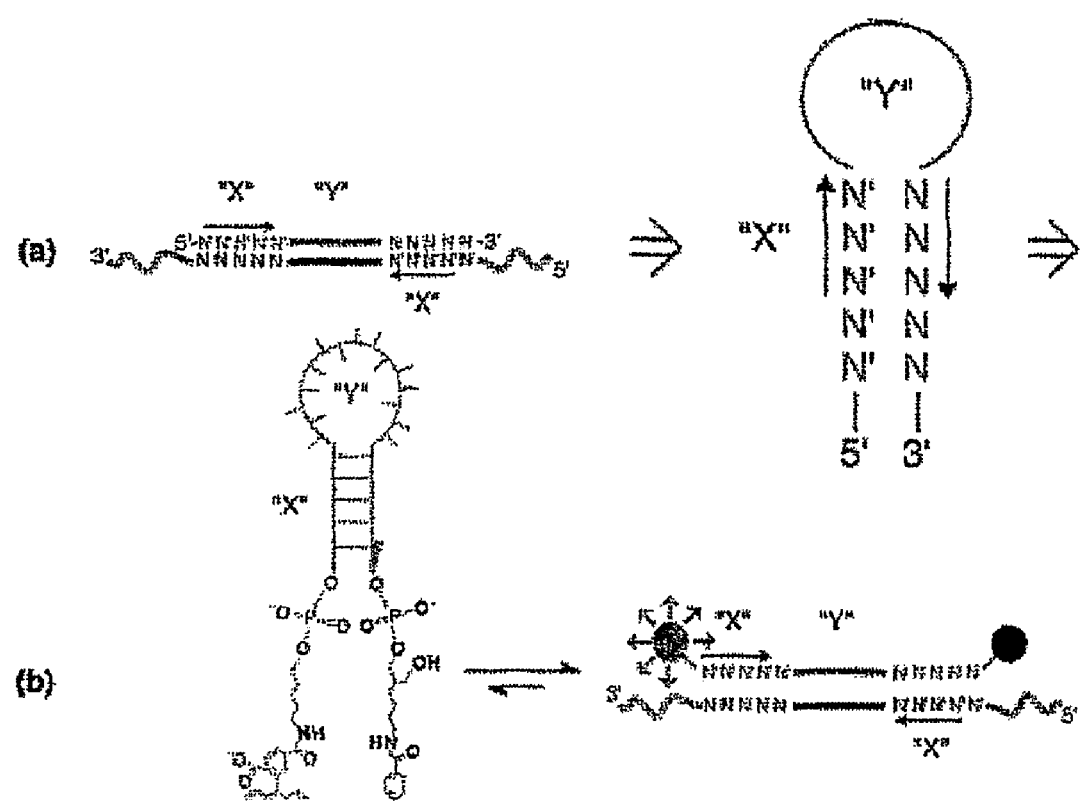
FIG. 1. SQRM design and reaction. (a) Concept: to exploit the traditional stem-loop structure of the SQRMs, a computer algorithm searched an entire sequence of mRNA for complementary sequences of a desired length (stems) that are separated by a proscribed distance (loop). (b) Chemistry: the complementary sequences were synthesized as SQRM possessing 50-fluorescein and 30 DABCYL groups. In the absence of target, quenching of fluorescence occurs. Once hybridization of the loop sequence to a complementary target takes place, the moieties are separated and fluorescence can be detected.

This invention provides methods of inducing apoptosis in a bcl-6-expressing cell and methods of treating a subject with a cancer comprising a bcl-6-expressing cell, comprising administration of a composition that reduces the amount of the bcl-6 protein or of an mRNA molecule encoding same, a composition comprising a nucleic acid molecule complementary to or corresponding to a region of the mRNA molecule, or a vector expressing the nucleic acid molecule. In another embodiment, the present invention provides an isolated nucleic acid molecule having a sequence corresponding to or complementary to accessible regions of bcl-6 mRNA, and vectors, cells, compositions, and kits comprising same.

In one embodiment, the present invention provides a method of inducing apoptosis in a bcl-6-expressing cell, comprising contacting the bcl-6-expressing cell with a composition that reduces an amount of the bcl-6 protein or of a ribonucleic acid (RNA) molecule encoding the bcl-6 protein, thereby inducing apoptosis in a bcl-6-expressing cell.

In one embodiment, the phrase "bcl-6 expressing" means that the cell expresses bcl-6 mRNA. In another embodiment, the phrase "bcl-6 expressing" means that the cell expresses bcl-6 protein. Methods of detecting expression of an mRNA are well known in the art, and include reverse transcription/polymerase chain reaction (PCR; Example 2), Western blotting (Example 2), fluorescence-activated cell sorting (FACS), and others. These methods are described, for example, in Sambrook et al., 2001, Molecular Cloning, A Laboratory Manual, Cold Spring Harbor Press, NY. Each method represents a separate embodiment of the present invention.

In another embodiment, the present invention provides a method of inducing apoptosis in a bcl-6-expressing cell, comprising contacting the bcl-6-expressing cell with a composition comprising a nucleic acid molecule complementary to a region of a RNA molecule encoding the bcl-6 protein, thereby inducing apoptosis in a bcl-6-expressing cell. In one embodiment, the region is an accessible region as defined herein.

As provided herein, the results demonstrate that bcl-6 contains regions that are available for hybridization, and that hybridization of complementary oligonucleotides to such regions of bcl-6 messenger RNA (mRNA) reduces levels of bcl-6 mRNA and bcl-6 protein and induces apoptosis in lymphoma cells.

In one embodiment, the bcl-6 transcript or mRNA of methods and compositions of the present invention has the sequence:

ggccctcgagcctcgaaccggaacctccaaatccgagacgctctgctta tgaggacctcgaaatatgccggccagtgaaaaaatcttatggctttgagg gcttttggttggccaggggcagtaaaaatctcggagagctgacaccaagt cctcccctgccacgtagcagtggtaaagccgaagctcaaattccgagaat tgagctctgttgattcttagaactggggttcttagaagtggtgatgcaag aagtttctaggaaaggccggacaccaggttttgagcaaaattttggactg tgaagcaaggcattggtgaagacaaaatggcctcgccggctgacagctgt atccagttcacccgccatgccagtgatgttcttctcaaccttaatcgtct ccggagtcgagacatcttgactgatgttgtcattgttgtgagccgtgagc agtttagagcccataaaacggtcctcatggcctgcagtggcctgttctat agcatcttacagaccagttgaaatgcaaccttagtgtgatcaatctaga tcctgagatcaaccctgagggattctgcatcctcctggacttcatgtaca catctcggctcaatttgcgggagggcaacatcatggctgtgatggccacg gctatgtacctgcagatggagcatgttgtggacacttgccggaagtttat taaggccagtgaagcagagatggtttctgccatcaagcctcctcgtgaag -continued

```
agttcctcaacagccggatgctgatgcccaagacatcatggcctatcgg
ggtcgtgaggtggtggagaacaacctgccactgaggagcgccctgggtg
tgagagcagagcctttgccccagcctgtacagtggcctgtccacaccgc
cagcctcttattccatgtacagccacctccctgtcagcagcctcctcttc
tccgatgaggagtttcgggatgtccggatgcctgtggccaaccccttccc
caaggagcgggcactcccatgtgatagtgccaggccagtccctggtgagt
acagccggccgactttggaggtgtccccaatgtgtgccacagcaatatc
tattcacccaaggaaacaatcccagaagaggcacgaagtgatatgcacta
cagtgtggctgagggcctcaaacctgctgcccctcagcccgaaatgccc
cctacttccttgtgacaaggccagcaaagaagaagagagaccctcctcg
gaagatgagattgccctgcatttcgagcccccaatgcacccctgaaccg
gaagggtctggttagtccacagagcccccagaaatctgactgccagccca
actcgcccacagaggcctgcagcagtaagaatgcctgcatcctccaggct
tctggctcccctccagccaagagcccactgaccccaaagcctgcaactg
gaagaaatacaagttcatcgtgctcaacagcctcaaccagaatgccaaac
caggggggcctgagcaggctgagctgggccgccttttcccacgagcctac
acggcccacctgcctgccagccacccatggagcctgagaaccttgacct
ccagtccccaaccaagctgagtgccagcggggaggactccaccatcccac
aagccagccggctctttaacatcgttaacaggtccatgacgggctctccc
cgcagcagcagcgagagccactcaccactctacatgcacccccgaagtg
cacgtcctgcggctctcagtccccacagcatgcagagatgtgcctccaca
ccgctggcccacgttcgctgaggagatgggagagaccagtctgagtac
tcagattctagctgtgagaacggggccttcttctgcaatgagtgtgactg
ccgcttctctgaggaggcctcactcaagaggcacacgctgcagacccaca
gtgacaaaccctacaagtgtgaccgctgccaggcctccttccgctacaag
ggcaacctcgccagccacaagaccgtccataccggtgagaaacctatcg
ttgcaacatctgtggggcccagttcaaccggccagccaacctgaaaaccc
acactcgaattcactctggagagaagccctacaaatgcgaaacctgcgga
gccagatttgtacaggtggcccacctccgtgcccatgtgcttatccacac
tggtgagaagccctatccctgtgaaatctgtggcaccccgtttccggcacc
ttcagactctgaagagccacctgcgaatccacacaggagagaaacccttac
cattgtgagaagtgtaacctgcatttccgtcacaaaagccagctgcgact
tcacttgcgccagaagcatggcgccatcaccaacaccaaggtgcaatacc
gcgtgtcagccactgacctgcctccggagctcccaaagcctgctgttgc
atggagtgttgatgctttcgtctccagcccctttctcagaatctacccaaa
ggatactgtaacactttacaatgttcatcccatgapttattgcctctttc
atccactagtgcaaatcatagctgggggttggggggtggtgggggtcgggg
cctggggactgggagccgcagcagctccccctccccactgccataaaa
cattaagaaaatcatattgcttcttctcctatgtgtaaggtgaaccatgt
cagcaaaaagcaaaatcattttatatgtcaaagcaggggagtatgcaaaa
gttctgacttgacttagtctgcaaaatgaggaatgtatatgttgttggga
acagatgttcttttgtatgtaaatgtgcattcttttaaaagacaagactt
cagtatgagtcaaagagagggctttaatttttttaaccaaaggtgaagga
atatatggcagagttgtaaatatataaatatatatatatataaaataaat
atatataaacctaacaaagatatattaaaaatataaaactgcgttaaagg
ctcgattttgtatctgcaggcagacacggatctgagaatctttattgaga
aagagcacttaagagaatattttaagtattgcatctgtataagtaagaaa
atattttgtctaaaatgcctcagtgtatttgtattttttgcaagtgaag
gtttacaatttacaaagtgtgtattaaaaaaaacccaaagaacccaaaaa
tctgcagaaggaaaaatgtgtaatttttgttctagttttcagtttgtatat
acccgtacaacgtgtcctcacggtgccttttttcacggaagttttcaatg
atgggcgagcgtgcaccatcccttttttgaagtgtaggcagacacagggac
ttgaagttgttactaactaaactctctttgggaatgtttgtctcatccca
ttctgcgtcatgcttgtgtgataactactccggagacagggtttggctgt
gtctaaactgcattaccgcgttgtaaaaaatagctgtaccaatataagaa
taaaatgttggaaagtcgcaaaaaaaaaaaa
```

(GenBank Accession Number U00115; SEQ ID No: 11).

In another embodiment, the bcl-6 transcript is represented by any of GenBank Accession Numbers NM_138931, NM_001706, NM_017745, NM_020926, AY316592, AK074286, AF317392, and AF317391. In another embodiment, the bcl-6 transcript comprises a sequence disclosed in any of GenBank Accession Numbers AF240680, AF240681, D38312, Z79581, and AF191831. In another embodiment, the bcl-6 transcript is represented by or contains any other bcl-6 sequence known in the art. In another embodiment, the bcl-6 transcript is a long isoform transcript. In another embodiment, the bcl-6 transcript is a short isoform transcript. In another embodiment, the bcl-6 transcript is spliced. In another embodiment, the bcl-6 transcript is not spliced. In another embodiment, the bcl-6 transcript is partially spliced. Each bcl-6 transcript represents a separate embodiment of the present invention.

In another embodiment, the bcl-6 transcript is a result of a translocation of the bcl-6 gene to another gene or region, e.g. the switch region ($S_H$) of the IgH locus. In one embodiment, the translocation comprises a sequence disclosed in any of GenBank Accession Numbers AJ557805 and AJ557817. In another embodiment, the bcl-6 transcript is a translocation of the bcl-6 gene to another gene or region. Each possibility represents a separate embodiment of the present invention.

In one embodiment, the complementary sequence is AGGCTGAGCTGGGCCGCCTTTCCCCACGAGCCT (segment 1190; SEQ ID No: 6). As shown in Example 1, an ODN corresponding to this sequence was able to bind bcl-6 RNA.

In another embodiment, the complementary sequence is GCTCTCCCCGCAGCAGCAGCGAGAGC (segment 1367; SEQ ID No: 7). In another embodiment, the complementary sequence is AAGCATGGAGTGTTGATGCTT (segment 2121; SEQ ID No: 10). As shown in Examples 2 and 3, antisense deoxynucleotides (ODN) corresponding to SQRM 1367, 1190, and 2121, and short interfering RNA (siRNA) corresponding to the complementary bcl-6 mRNA sequence, decreased the bcl-6 expression and reduced the viability of lymphoma cells. Thus, such nucleotides have utility in inducing apoptosis in bcl-6 expressing cells and treating lymphomas.

In another embodiment, the complementary sequence is GCTGAGGGCCTCAAACCTGCTGCCCCCTCAGC (segment 831; SEQ ID No: 4). In another embodiment, the complementary sequence is any of the other target sequences listed in Table 1.

In another embodiment, the present invention provides a method of inducing apoptosis in a bcl-6-expressing cell, comprising contacting the bcl-6-expressing cell with a composition comprising a nucleic acid molecule corresponding to a region of an RNA molecule encoding the bcl-6 protein, thereby inducing apoptosis in a bcl-6-expressing cell. As shown in Example 3, administration of siRNA corresponding to regions of bcl-6 mRNA decreased the bcl-6 expression and reduced the viability of lymphoma cells.

In another embodiment, the present invention provides a method of inducing apoptosis in a bcl-6-expressing cell, comprising contacting the bcl-6-expressing cell with a vector expressing a nucleic acid molecule complementary to a region of a RNA molecule encoding the bcl-6 protein, thereby inducing apoptosis in a bcl-6-expressing cell.

In another embodiment, the present invention provides a method of inducing apoptosis in a bcl-6-expressing cell, comprising contacting the bcl-6-expressing cell with a vector expressing a nucleic acid molecule corresponding to a region of a RNA molecule encoding the bcl-6 protein, thereby inducing apoptosis in a bcl-6-expressing cell.

Methods of detecting apoptosis are well known in the art, and include trypan blue staining (Example 2), ethidium bromide/acridine orange staining (Example 4), TUNEL assay, magnetic resonance (Brindle K M, Br J Radiol 76 Spec No 2:S111-7, 2003), and the use of radioactive ligands (Lahorte C M et al, Eur J Nucl Med Mol Imaging 31(6):887-919, 2004), and are described, for example, in Mirakian R et al, J Immunol Methods 265(1-2):161-75, 2002. Each method represents a separate embodiment of the present invention.

In one embodiment, the target cell of methods of the present invention is a lymphoma cell. In another embodiment, the cell is a non-Hodgkin's lymphoma cell. In another embodiment, the cell is a type of cancer cell other than lymphoma. In another embodiment, the cell is any other type of cell that expresses bcl-6 protein or mRNA. Each possibility represents a separate embodiment of the present invention.

In another embodiment, the present invention provides a method of treating a subject with a cancer comprising a bcl-6-expressing cell, comprising contacting the subject with a composition that reduces an amount of the bcl-6 protein or of a RNA molecule encoding the bcl-6 protein, thereby treating a subject with cancer comprising a bcl-6-expressing cell.

In another embodiment, the present invention provides a method of treating a subject with a cancer comprising a bcl-6-expressing cell, comprising contacting the subject with a composition comprising a nucleic acid molecule complementary to a region of a RNA molecule encoding the bcl-6 protein, thereby treating a subject with cancer comprising a bcl-6-expressing cell.

In another embodiment, the present invention provides a method of treating a subject with a cancer comprising a bcl-6-expressing cell, comprising contacting the subject with a composition comprising a nucleic acid molecule corresponding to a region of a RNA molecule encoding the bcl-6 protein, thereby treating a subject with cancer comprising a bcl-6-expressing cell.

In another embodiment, the present invention provides a method of treating a subject with a cancer comprising a bcl-6-expressing cell, comprising contacting the subject with a vector expressing a nucleic acid molecule complementary to a region of a RNA molecule encoding the bcl-6 protein, thereby treating a subject with cancer comprising a bcl-6-expressing cell.

In another embodiment, the present invention provides a method of treating a subject with a cancer comprising a bcl-6-expressing cell, comprising contacting the subject with a vector expressing a nucleic acid molecule corresponding to a region of a RNA molecule encoding the bcl-6 protein, thereby treating a subject with cancer comprising a bcl-6-expressing cell.

In one embodiment, the cancer is a lymphoma. In another embodiment, the cancer is another cancer. Each possibility represents a separate embodiment of the present invention. As shown in Example 4, lentiviruses expressing short hairpin sequences complementary to bcl-6 mRNA decrease viability of lymphoma cells and their bcl-6 expression. Thus, such lentiviruses have utility in treating lymphoma.

A large number of vectors known in the art may be used in methods and compositions of the present invention. A vector may include, in some embodiments, an appropriate selectable marker. In other embodiments, the vector may further include an origin of replication, or may be a shuttle vector, which can propagate both in bacteria, such as, for example, *E. coli* (wherein the vector comprises an appropriate selectable marker and origin of replication) or be compatible for propagation in vertebrate cells, or integration in the genome of an organism of choice. The vector according to this aspect of the present invention may be, for example, a plasmid, a bacmid, a phagemid, a cosmid, a phage, a modified or unmodified virus, an artificial chromosome, or any other vector known in the art. Many such vectors are commercially available, and their use is well known to those skilled in the art (see, for example, Molecular Cloning, (2001), Sambrook and Russell, eds.). Each vector represents a separate embodiment of the present invention.

In another embodiment, the nucleotide molecule present in the vector may be a plasmid, cosmid, or the like, or a vector or strand of nucleic acid. In another embodiment, the nucleotide molecule may be genetic material of a living organism, virus, phage, or material derived from a living organism, virus, or phage. The nucleotide molecule may be, in one embodiment, linear, circular, or concatemerized, and may be of any length. Each type of nucleotide molecule represents a separate embodiment of the present invention.

In another embodiment, nucleic acid vectors comprising the isolated nucleic acid sequence include a promoter for regulating expression of the isolated nucleic acid. Such promoters are known to be cis-acting sequence elements required for transcription, as they serve to bind DNA-dependent RNA polymerase, which transcribes sequences present downstream thereof. Each vector represents a separate embodiment of the present invention.

In one embodiment, the isolated nucleic acid is subcloned into the vector. "Subcloning" refers, in one embodiment, to inserting an oligonucleotide into a nucleotide molecule. In one embodiment isolated DNA encoding an RNA transcript is inserted into an appropriate expression vector that is suitable for the host cell such that the DNA is transcribed to produce the RNA.

The insertion into a vector can, in another embodiment, be accomplished by ligating the DNA fragment into a vector that has complementary cohesive termini. However, if the complementary restriction sites used to fragment the DNA are not present in the cloning vector, the ends of the DNA molecules are, in another embodiment, enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. Methods for subcloning are known to those skilled in the art, and are described, for example in Molecular Cloning, (2001), Sambrook and Russell, eds. Each method represents a separate embodiment of the present invention.

In one embodiment, the lymphoma is a follicular lymphoma. In another embodiment, the lymphoma is a Burkitt's lymphoma/Burkitt's cell leukemia. In another embodiment, the lymphoma is a diffuse large B-cell lymphoma. In another embodiment, the lymphoma is a precursor B-cell neoplasm. In another embodiment, the lymphoma is a mature (peripheral) B-cell neoplasm. In another embodiment, the lymphoma is a B-cell chronic lymphocytic leukemia/small lymphocytic lymphoma. In another embodiment, the lymphoma is a B-cell prolymphocytic leukemia. In another embodiment, the lymphoma is a lymphoplasmacytic lymphoma. In another embodiment, the lymphoma is a splenic marginal zone B-cell lymphoma, including villous lymphocytes. In another embodiment, the lymphoma is a splenic marginal zone B-cell lymphoma, not including villous lymphocytes. In another embodiment, the lymphoma is a nodal marginal zone lymphoma, including monocytoid B-cells. In another embodiment, the lymphoma is a nodal marginal zone lymphoma, not including monocytoid B-cells. In another embodiment, the lymphoma is an extranodal marginal zone B-cell lymphoma of the mucosa-associated lymphoid tissue (MALT) type. In another embodiment, the lymphoma is a hairy cell leukemia. In another embodiment, the lymphoma is a plasma cell myeloma/plasmacytoma. In another embodiment, the lymphoma is a mantle cell lymphoma. In another embodiment, the lymphoma is a mediastinal large B-cell lymphoma. In another embodiment, the lymphoma is an intravascular large B-cell lymphoma. In another embodiment, the lymphoma is a primary effusion lymphoma. In another embodiment, the lymphoma is a lymphomatoid granulomatosis. In another embodiment, the lymphoma is a post-transplant lymphoproliferative disorder. In another embodiment, the lymphoma is a T-cell neoplasm. In another embodiment, the lymphoma is a Natural Killer (NK) cell neoplasm. In another embodiment, the lymphoma is a precursor T cell neoplasm. In another embodiment, the lymphoma is a precursor T-lymphoblastic lymphoma/leukemia. In another embodiment, the lymphoma is a blastic NK lymphoma. In another embodiment, the lymphoma is a mature (peripheral) T cell neoplasm. In another embodiment, the lymphoma is a mature NK-cell neoplasm. In another embodiment, the lymphoma is a T-cell prolymphocytic leukemia. In another embodiment, the lymphoma is a T-cell granular lymphocytic leukemia. In another embodiment, the lymphoma is an aggressive NK cell leukemia. In another embodiment, the lymphoma is an (HTLV1+) Adult T cell lymphoma/leukemia. In another embodiment, the lymphoma is an extranodal NK/T-cell lymphoma of the nasal type. In another embodiment, the lymphoma is an enteropathy-type T-cell lymphoma. In another embodiment, the lymphoma is a hepatosplenic gamma-delta T-cell lymphoma. In another embodiment, the lymphoma is a subcutaneous panniculitis-like T-cell lymphoma. In another embodiment, the lymphoma is a mycosis fungoides/S'zary's syndrome. In another embodiment, the lymphoma is a primary cutaneous anaplastic large cell lymphoma of the T cell variety. In another embodiment, the lymphoma is a primary cutaneous anaplastic large cell lymphoma of the null cell variety. In another embodiment, the lymphoma is an unspecified peripheral T cell lymphoma. In another embodiment, the lymphoma is an angioimmunoblastic T cell lymphoma. In another embodiment, the lymphoma is a primary systemic anaplastic large cell lymphoma of the T cell variety. In another embodiment, the lymphoma is a primary systemic anaplastic large cell lymphoma of the null cell variety. In another embodiment, the lymphoma is a lymphomatoid papulosis. In another embodiment, the lymphoma is an intermediate grade lymphoma. In another embodiment, the lymphoma is a high grade lymphoma. In another embodiment, the lymphoma is an indolent lymphoma. In another embodiment, the lymphoma is an aggressive lymphoma. In another embodiment, the lymphoma is any other type of lymphoma known in the art. Each type of lymphoma represents a separate embodiment of the present invention.

In another embodiment, the present invention provides an isolated nucleic acid molecule having a sequence selected from the sequences set forth in SEQ ID No: 1-10. In another embodiment, the present invention provides an isolated nucleic acid molecule having a sequence complementary to a sequence selected from the sequences set forth in SEQ ID No: 1-10.

In another embodiment, the present invention provides an siRNA molecule having a sequence corresponding to a fragment of an isolated nucleic acid molecule of the present invention. In one embodiment, the fragment is about 21-23 nucleotide in length. In another embodiment, the fragment is an accessible fragment.

In another embodiment, the present invention provides an shRNA molecule comprising a sequence corresponding to a fragment of an isolated nucleic acid molecule of the present invention. In one embodiment, the fragment is about 19-23 nucleotide in length. In another embodiment, the fragment is an accessible fragment.

In another embodiment, the present invention provides an ODN molecule having a sequence corresponding to an isolated nucleic acid molecule of the present invention or a fragment thereof. In one embodiment, the fragment is about 21-23 nucleotide in length. In another embodiment, the fragment is an accessible fragment.

In one embodiment, the length of the fragment of the isolated nucleic acid molecule wherefrom an ODN, siRNA, or shRNA of the present invention is derived is 21-23 nucleotides. In another embodiment, the fragment is about 19 nucleotide in length. In another embodiment, the fragment is about 21 nucleotide in length. In another embodiment, the fragment is about 23 nucleotide in length. In another embodiment, the fragment is about 25 nucleotide in length.

In one embodiment, the nucleic acid molecule of methods and compositions of the present invention is an oligo-deoxyribonucleic acid (ODN) molecule. short interfering RNA (siRNA) molecule; short hairpin RNA (shRNA) In another embodiment, the nucleic acid molecule is any other type of nucleic acid molecule known in the art.

In one embodiment, the nucleotide of methods and compositions of the present invention is an antisense nucleotide. In one embodiment, the antisense nucleotide is an antisense RNA. In another embodiment, the antisense nucleotide is an siRNA. In another embodiment, the antisense nucleotide is a short hairpin RNA (shRNA). siRNA and shRNA are short RNA sequences that induce sequence-specific RNA degradation when introduced into a cell. The use of siRNA and hairpin RNA is well known in the art, and is described, for example, in Yu J et al (Proc Natl Acad Sci 99(9): 6047-52, 2002). In another embodiment, the antisense nucleotide is a ribozyme. In another embodiment, the antisense nucleotide is a DNAzyme. In another embodiment, the antisense nucleotide is an antisense DNA. In another embodiment, the antisense nucleotide is any other type of nucleic acid molecule capable of destabilizing mRNA known in the art. Each possibility represents a separate embodiment of the present invention.

In another embodiment, "nucleic acid" refers to a string of at least two base-sugar-phosphate combinations. The term includes, in one embodiment, DNA and RNA. "Nucleotides" refers, in one embodiment, to the monomeric units of nucleic acid polymers. RNA may be, in another embodiment, in the form of a tRNA (transfer RNA), snRNA (small nuclear RNA), rRNA (ribosomal RNA), micro RNA (miRNA) and ribozymes. The use of siRNA and miRNA has been described (Caudy A A et al, Genes & Devel 16: 2491-96 and references cited therein). DNA may be in form of plasmid DNA, viral DNA, linear DNA, or chromosomal DNA or derivatives of these groups. In addition, these forms of DNA and RNA may be single, double, triple, or quadruple stranded. The term also includes, in another embodiment, artificial nucleic acids that may contain other types of backbones but the same bases. In one embodiment, the artificial nucleic acid is a PNA (peptide nucleic acid). In another embodiment, the nucleotide is oxetane modified. In another embodiment, the nucleotide is modified by replacement of one or more phosphodiester bonds with a phosphorothioate bond (Example 2). PNA contain peptide backbones and nucleotide bases and are able, in one embodiment, to bind both DNA and RNA molecules. In another embodiment, the artificial nucleic acid contains any other variant of the phosphate backbone of native nucleic acids known in the art. The use of phosphothiorate nucleic acids and PNA are known to those skilled in the art, and are described in, for example, Neilsen P E, Curr Opin Struct Biol 9:353-57; and Raz N K et at Biochem Biophys Res Commun. 297:1075-84. The production and use of nucleic acids is known to those skilled in art and is described, for example, in Molecular Cloning, (2001), Sambrook and Russell, eds. and Methods in Enzymology: Methods for molecular cloning in eukaryotic cells (2003) Purchio and G. C. Fareed, eds. Each nucleic acid derivative represents a separate embodiment of the present invention.

In another embodiment, the nucleotide molecule of methods and compositions of the present invention is homologous to a nucleotide molecule disclosed herein. The terms "homology," "homologous," etc, when in reference to any protein or peptide, refer, in one embodiment, to a percentage of amino acid residues in the candidate sequence that are identical with the residues of a corresponding native polypeptide, after aligning the sequences and introducing gaps, if necessary, to achieve the maximum percent homology, and not considering any conservative substitutions as part of the sequence identity. Methods and computer programs for the alignment are well known in the art.

In another embodiment, the term "homology," when in reference to any nucleic acid sequence similarly indicates a percentage of nucleotides in a candidate sequence that are identical with the nucleotides of a corresponding native nucleic acid sequence.

Homology is, in one embodiment, determined by computer algorithm for sequence alignment, by methods well described in the art. For example, computer algorithm analysis of nucleic acid sequence homology may include the utilization of any number of software packages available, such as, for example, the BLAST, DOMAIN, BEAUTY (BLAST Enhanced Alignment Utility), GENPEPT and TREMBL packages.

In another embodiment, "homology" refers to identity to a sequence selected from SEQ ID No: 1-11 of greater than 70%. In another embodiment, "homology" refers to identity to a sequence selected from SEQ ID No: 1-11 of greater than 72%. In another embodiment, "homology" refers to identity to one of SEQ ID No: 1-11 of greater than 75%. In another embodiment, "homology" refers to identity to a sequence selected from SEQ ID No: 1-11 of greater than 78%. In another embodiment, "homology" refers to identity to one of SEQ ID No: 1-11 of greater than 80%. In another embodiment, "homology" refers to identity to one of SEQ ID No: 1-11 of greater than 82%. In another embodiment, "homology" refers to identity to a sequence selected from SEQ ID No: 1-11 of greater than 83%. In another embodiment, "homology" refers to identity to one of SEQ ID No: 1-11 of greater than 85%. In another embodiment, "homology" refers to identity to one of SEQ ID No: 1-11 of greater than 87%. In another embodiment, "homology" refers to identity to a sequence selected from SEQ ID No: 1-11 of greater than 88%. In another embodiment, "homology" refers to identity to one of SEQ ID No: 1-11 of greater than 90%. In another embodiment, "homology" refers to identity to one of SEQ ID No: 1-11 of greater than 92%. In another embodiment, "homology" refers to identity to a sequence selected from SEQ ID No: 1-11 of greater than 93%. In another embodiment, "homology" refers to identity to one of SEQ ID No: 1-11 of greater than 95%. In another embodiment, "homology" refers to identity to a sequence selected from SEQ ID No: 1-11 of greater than 96%. In another embodiment, "homology" refers to identity to one of SEQ ID No: 1-11 of greater than 97%. In another embodiment, "homology" refers to identity to one of SEQ ID No: 1-11 of greater than 98%. In another embodiment, "homology" refers to identity to one of SEQ ID No: 1-11 of greater than 99%. In another embodiment, "homology" refers to identity to one of SEQ ID No: 1-11 of 100%.

In another embodiment, homology is determined is via determination of candidate sequence hybridization, methods of which are well described in the art (See, for example, "Nucleic Acid Hybridization" Hames, B. D., and Higgins S. J., Eds. (1985); Sambrook et al., 2001, Molecular Cloning, A Laboratory Manual, Cold Spring Harbor Press, NY; and Ausubel et al., 1989, Current Protocols in Molecular Biology, Green Publishing Associates and Wiley Interscience, N.Y). For example methods of hybridization may be carried out under moderate to stringent conditions, to the complement of a DNA encoding a native caspase peptide. Hybridization conditions being, for example, overnight incubation at 42° C. in a solution comprising: 10-20% formamide, 5×SSC (150 mM NaCl, 15 mM trisodium citrate), 50 mM sodium phosphate (pH 7.6), 5× Denhard's solution, 10% dextran sulfate, and 20 μg/ml denatured, sheared salmon sperm DNA.

Protein and/or peptide homology for any amino acid sequence listed herein is determined, in one embodiment, by methods well described in the art, including immunoblot analysis, or via computer algorithm analysis of amino acid sequences, utilizing any of a number of software packages available, via established methods. Some of these packages may include the FASTA, BLAST, MPsrch or Scanps packages, and may employ the use of the Smith and Waterman algorithms, and/or global/local or BLOCKS alignments for analysis, for example. Each method of determining homology represents a separate embodiment of the present invention.

In another embodiment, the present invention provides a composition comprising an isolated nucleic acid molecule of the present invention.

In another embodiment, the present invention provides a vector comprising an isolated nucleic acid molecule of the present invention. In another embodiment, the present invention provides a composition comprising a vector of the present invention.

In another embodiment, the present invention provides a cell comprising an isolated nucleic acid molecule of the present invention. In another embodiment, the present invention provides a composition comprising a cell of the present invention.

In another embodiment, the present invention provides a kit comprising a reagent utilized in performing a method of the present invention. In another embodiment, the present invention provides a kit comprising an isolated nucleic acid of the present invention. In another embodiment, the present invention provides a kit comprising a vector of the present invention. In another embodiment, the present invention provides a kit comprising a cell of the present invention. In another embodiment, the present invention provides a kit comprising a composition of the present invention.

In another embodiment, a method of the present invention is used to treat minimal or residual lymphoma. Methods for detecting minimal lymphoma are well known in the art, and are described, for example in Sharp J G et al (Cancer Metastasis Rev 18(1): 127-42, 1999). Each method represents a separate embodiment of the present invention.

In one embodiment, a treatment protocol of the present invention is therapeutic. In another embodiment, the protocol is prophylactic. In one embodiment, a composition of the present invention may be administered to a subject having a cancer that does not comprise a bcl-6 expressing cell, to prevent the development of bcl-6-expressing clones of the cancer. Each possibility represents a separate embodiment of the present invention.

In another embodiment, a method of the present invention utilizes an siRNA or shRNA not disclosed herein that is derived from an accessible region of the bcl-6 mRNA. Examples 5 and 6 describe methods of generation and testing of novel siRNA or shRNA derived from an accessible region of the bcl-6 mRNA.

In another embodiment, the present invention provides the use of a composition that reduces an amount of the bcl-6 protein or of a RNA molecule encoding the bcl-6 protein in the manufacture of a medicament for treating a cancer comprising a bcl-6-expressing cell.

In another embodiment, the present invention provides the use of a composition comprising a nucleic acid molecule complementary to a region of a RNA molecule encoding the bcl-6 protein in the manufacture of a medicament for treating a cancer comprising a bcl-6-expressing cell.

In another embodiment, the present invention provides the use of a composition comprising a nucleic acid molecule corresponding to a region of a RNA molecule encoding the bcl-6 protein in the manufacture of a medicament for treating a cancer comprising a bcl-6-expressing cell.

In another embodiment, the present invention provides the use of a vector expressing a nucleic acid molecule complementary to a region of a RNA molecule encoding the bcl-6 protein in the manufacture of a medicament for treating a cancer comprising a bcl-6-expressing cell.

In another embodiment, the present invention provides the use of a vector expressing a nucleic acid molecule corresponding to a region of a RNA molecule encoding the bcl-6 protein in the manufacture of a medicament for treating a cancer comprising a bcl-6-expressing cell.

In one embodiment, the term "contacting" or "administering" refers to a method of exposure, which may be direct or indirect. In one method such contact comprises direct injection of a cell or tumor through any means well known in the art, such as microinjection. It is also envisaged, in another embodiment, that supply to the cell or tumor is indirect, such as via administration to a subject, provision in a culture medium that surrounds the cell, or via any route known in the art. In another embodiment, the term "contacting" means that the nucleotide molecule of the present invention is introduced into a subject receiving treatment, and the nucleotide molecule is allowed to come in contact with the tumor in vivo.

In another embodiment, "contacting" refers to introducing the anti-estrogen compound of the present invention into a sample containing the enzyme in a test tube, flask, tissue culture, chip, array, plate, microplate, capillary, or the like, and incubated at a temperature and time sufficient to permit uptake of the nucleotide molecule by the cell. Methods for contacting the samples with the nucleotide are known to those skilled in the art and may be selected depending on the type of assay protocol to be run. Incubation methods are also known to those skilled in the art. Each possibility represents a separate embodiment of the present invention.

Pharmaceutical Compositions

"Pharmaceutical composition" refers, in one embodiment, to a therapeutically effective amount of the active ingredient, i.e. the nucleotide, together with a pharmaceutically acceptable carrier or diluent. A "therapeutically effective amount" refers, in one embodiment, to that amount which provides a therapeutic effect for a given condition and administration regimen.

The pharmaceutical compositions containing the nucleotide can be administered to a subject by any method known to a person skilled in the art, such as intra-tumorally, parenterally, paracancerally, transmucosally, transdermally, intramuscularly, intravenously, intra-dermally, subcutaneously, intra-peritonealy, intra-ventricularly, intra-cranially, or intra-vaginally.

In one embodiment, the pharmaceutical compositions are administered orally, and are thus formulated in a form suitable for oral administration, i.e. as a solid or a liquid preparation. Suitable solid oral formulations include tablets, capsules, pills, granules, pellets and the like. Suitable liquid oral formulations include solutions, suspensions, dispersions, emulsions, oils and the like. In one embodiment of the present invention, the nucleotide molecules are formulated in a capsule. In accordance with this embodiment, the compositions of the present invention comprise, in addition to the nucleotide active compound and the inert carrier or diluent, a hard gelating capsule.

Further, in another embodiment, the pharmaceutical compositions are administered by intravenous, intraarterial, or intramuscular injection of a liquid preparation. Suitable liquid formulations include solutions, suspensions, dispersions, emulsions, oils and the like. In one embodiment, the pharmaceutical compositions are administered intravenously and are thus formulated in a form suitable for intravenous administration. In another embodiment, the pharmaceutical compositions are administered intraarterially and are thus formulated in a form suitable for intraarterial administration. In another embodiment, the pharmaceutical compositions are administered intramuscularly and are thus formulated in a form suitable for intramuscular administration.

Further, in another embodiment, the pharmaceutical compositions are administered topically to body surfaces and are thus formulated in a form suitable for topical administration. Suitable topical formulations include gels, ointments, creams, lotions, drops and the like. For topical administration, the nucleotide agents or their physiologically tolerated derivatives such as salts, esters, N-oxides, and the like are prepared and applied as solutions, suspensions, or emulsions in a physiologically acceptable diluent with or without a pharmaceutical carrier.

Further, in another embodiment, the pharmaceutical compositions are administered as a suppository, for example a rectal suppository or a urethral suppository. Further, in another embodiment, the pharmaceutical compositions are administered by subcutaneous implantation of a pellet. In a further embodiment, the pellet provides for controlled release of nucleotide agent over a period of time.

In another embodiment, the active compound is delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 3 17-327; see generally ibid).

As used herein "pharmaceutically acceptable carriers or diluents" are well known to those skilled in the art. The carrier or diluent may be a solid carrier or diluent for solid formulations, a liquid carrier or diluent for liquid formulations, or mixtures thereof.

Solid carriers/diluents include, but are not limited to, a gum, a starch (e.g. corn starch, pregeletanized starch), a sugar (e.g., lactose, mannitol, sucrose, dextrose), a cellulosic material (e.g. microcrystalline cellulose), an acrylate (e.g. polymethylacrylate), calcium carbonate, magnesium oxide, talc, or mixtures thereof.

For liquid formulations, pharmaceutically acceptable carriers may be aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of petroleum, animal, vegetable, or synthetic origin, for example, peanut oil, soybean oil, mineral oil, olive oil, sunflower oil, and fish-liver oil.

Parenteral vehicles (for subcutaneous, intravenous, intraarterial, or intramuscular injection) include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions. Examples of oils are those of petroleum, animal, vegetable, or synthetic origin, for example, peanut oil, soybean oil, mineral oil, olive oil, sunflower oil, and fish-liver oil.

In addition, the compositions may further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmellose sodium, crospovidone, guar gum, sodium starch glycolate), buffers (e.g., Tris-HCl., acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., glycerol, polyethylene glycerol), anti-oxidants (e.g., ascorbic acid, sodium metabisulfite, butylated hydroxyanisole), stabilizers (e.g. hydroxypropyl cellulose, hydroxypropylmethyl cellulose), viscosity increasing agents (e.g. carbomer, colloidal silicon dioxide, ethyl cellulose, guar gum), sweeteners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates) and/or adjuvants.

In one embodiment, the pharmaceutical compositions provided herein are controlled-release compositions, i.e. compositions in which the nucleotide molecule is released over a period of time after administration. Controlled- or sustained-release compositions include formulation in lipophilic depots (e.g. fatty acids, waxes, oils). In another embodiment, the composition is an immediate-release composition, i.e. a composition in which all of the nucleotide molecule is released immediately after administration.

In another embodiment, the pharmaceutical composition can be delivered in a controlled release system. For example, the agent may be administered using intravenous infusion, an implantable osmotic pump, a transdermal patch, liposomes, or other modes of administration. In one embodiment, a pump may be used (see Langer, supra; Sefton, C R C Crit. Ref. Biomed. Eng. 14:201 (1987); Buchwald et al., Surgery 88:507 (1980); Saudek et al., N. Engl. J. Med. 321:574 (1989). In another embodiment, polymeric materials can be used. In yet another embodiment, a controlled release system can be placed in proximity to the therapeutic target, i.e., the brain, thus requiring only a fraction of the systemic dose (see, e.g., Goodson, in Medical Applications of Controlled Release, supra, vol. 2, pp. 115-138 (1984). Other controlled-release systems are discussed in the review by Langer (Science 249:1527-1533 (1990).

The compositions also includes, in one embodiment, incorporation of the active material into or onto particulate preparations of polymeric compounds such as polylactic acid, polyglycolic acid, hydrogels, etc, or onto liposomes, microemulsions, micelles, unilamellar or multilamellar vesicles, erythrocyte ghosts, or spheroplasts.) Such compositions will influence the physical state, solubility, stability, rate of in vivo release, and rate of in vivo clearance.

Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors.

Also comprehended by the invention are compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. The modified compounds are known to exhibit substantially longer half-lives in blood following intravenous injection than do the corresponding unmodified compounds (Abuchowski et al., 1981; Newmark et al., 1982; and Katre et al., 1987). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

The preparation of pharmaceutical compositions that contain an active component, for example by mixing, granulating, or tablet-forming processes, is well understood in the art. The active therapeutic ingredient is often mixed with excipients that are pharmaceutically acceptable and compatible with the active ingredient. For oral administration, the nucleotide agents or their physiologically tolerated derivatives such as salts, esters, N-oxides, and the like are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions. For parenteral administration, the nucleotide agents or their physiologically tolerated derivatives such as salts, esters, N-oxides, and the like are converted into a solution, suspension, or emulsion, if desired with the substances customary and suitable for this purpose, for example, solubilizers or other substances.

An active component can be formulated into the composition as neutralized pharmaceutically acceptable salt forms. Pharmaceutically acceptable salts include the acid addition salts (formed with the free amino groups of the polypeptide or antibody molecule), which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

For use in medicine, the salts of the nucleotides are pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts, which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic: acid, oxalic acid, citric acid, tartaric acid, carbonic acid or phosphoric acid. Each pharmaceutical carrier or excipient represents a separate embodiment of the present invention.

In one embodiment, the term "treating" refers to curing a disease. In another embodiment, "treating" refers to preventing a disease. In another embodiment, "treating" refers to reducing the incidence of a disease. In another embodiment, "treating" refers to inducing remission. In another embodiment, "treating" refers to slowing the progression of a disease. The terms "reducing", "suppressing" and "inhibiting" refer in one embodiment, to lessening or decreasing. The term "progression" may refers to increasing in scope or severity, advancing, growing or becoming worse. The term "recurrence" refers, in one embodiment, to the return of a disease after a remission.

In one embodiment, the term "administering" refers to bringing a subject in contact with a nucleotide molecule of the present invention. In another embodiment, administration is accomplished in vitro, i.e. in a test tube. In another embodiment, administration is accomplished in vivo, i.e. in cells or tissues of a living organism. Each possibility represents a separate embodiment of the present invention.

In one embodiment, the methods of the present invention comprise administering an nucleotide molecule as the sole active ingredient. However, also encompassed within the scope of the present invention are methods that comprise administering the nucleotide molecules in combination with one or more therapeutic agents. These agents include, but are not limited to, various cancer chemotherapy agents and other pharmaceutical compounds known in the art to be administered together with cancer chemotherapy agents.

EXPERIMENTAL DETAILS SECTION

Example 1

Identification of Accessible Regions of Bcl-6 RNA

Materials and Experimental Methods

Cells

Bcl-6 expressing Louckes cells were obtained from Jill Lacy, Yale University. K562 cells were used as a negative control for cells not expressing bcl-6. Cells were maintained in RPMI 1640 media supplemented with 10% FBS and 0.5% penicillin/streptomycin.

Cloning and In Vitro Transcription

An insert containing full length (2.4 kilobase) bcl-6 coding sequence, obtained from R. Dalla-Favera, Columbia University) was sub-cloned into a pcDNA3 plasmid (Invitrogen, Carlsbad, Calif.) using the KpnI and HindIII cloning sites. RNA was transcribed from linearized plasmids using the T7 RNA Polymerase RiboMax™ Kit (Promega). Transcribed bcl-6 mRNA was used for subsequent experiments.

ODNs and Synthesis of SQRM

SQRM ODNs were synthesized in the University of Pennsylvania Cancer Center Nucleic Acid Facility on an ExpediteTM8909 Nucleic Acid Synthesis System (Applied Biosystems) using standard phosphoramidite chemistry; bcl-6 antisense ODNs were (AS ODNs) obtained from Integrated DNA Technologies]. The SQRM complements to the Access-Search outputted RNA sequences are synthesized with 30-C7-4-(4'-dimethylaminophenylazo)benzoic acid (DABCYL) Controlled Pore Glass (Glen Research) used as support and a fluoresceinphosphoramidite (Cruachem) for 5' end modification (Table 1). All ODNs and SQRMs were HPLC-purified. SQRMs were numbered according to the following convention: the SQRM's number designator corresponds to the 5' base of mRNA to which the 3' base of the SQRM complements, the adenine of the initiation codon is base (+1), and the base 5' of the initiation A is designated (−1), no zero base. The full descriptor is characterized by the number of the first 5' RNA base involved in a duplex with the probe, an arrow to indicate the direction of hybridization of the probe to the mRNA and a second number that corresponds to the 3'-most base involved in the helix.

Fluorescence Hybridization Assays

SQRMs (100 nM) were incubated for 30 min at 37° C. with (1 mM) in vitro transcribed RNA, (10 mM) complementary ODN (positive control) or (1 mM) scrambled ODN (negative control) target in SQRM buffer (100 mM Tris-HCl, pH 7.5, 2 mM $MgCl_2$). 'Scrambled' ODNs were designed by replacing each base with its complementary base in the same 5' to 3' direction. The fluorescence was monitored in a plate reader equilibrated to 37° C. Signal-to-noise ratios for all reactions can be found in Table 2.

Total RNA was isolated from Louckes cells and K562 cells with QIAgen RNeasy Kit (Qiagen). Fluorescence emission was monitored using a Packard FluoroCount Microplate Fluorometer (Packard Instrument Company).

RNaseH Cleaving Assay

1 µM of SQRM was pre-incubated with 1 µM bcl-6 mRNA in the presence of 100 mM Tris and 2 mM MgCl at 37° C. for 10 min to allow hybridization to occur. RNaseH buffer and enzyme were added, and the mixture was incubated for another 10 min at 37° C. The reaction was stopped by adding Proteinase K, and the whole reaction mixture was resolved on a 1% agarose gel. In this case the bcl-6 mRNA was generated by rabbit reticulocyte lysate transcription/translation system. This system was employed to model the effect that cellular proteins might have on ODN hybridization. Equal amounts of post-translation product from each reaction mixture were analyzed by electrophoresis in a single polyacrylamide gel, followed by PhosphorImager® analysis.

Preparation of Total Cellular RNA

Total RNA was isolated from cells using a Qiagen (Valencia, Calif.) mini kit, and the yield measured spectrophotometry. A total amount of 20,000 µg and 40,000 µg RNA was incubated in the fluorimeter with SQRM and compared with background fluorescence, fluorescence of the negative control, and fluorescence of the SQRM with 1 µg in vitro-transcribed bcl-6 RNA.

Results

In order to identify regions of bcl-6 RNA that are accessible to hybridization, a computer-driven search algorithm was used to identify 20-35 base pair (bp) sequences with palindromic regions of 4-6 bp in length, within the bcl-6 sequence. 10 such sequences were identified, and SQRM complementary to the sequences were designed; these are depicted in Table 1. FIG. 1 shows a schematic depiction of the SQRM mechanism.

Table 1: SQRM sequences. In each case, the SQRM was modified with fluorescein on the 5' end and DABCYL on the 3' end.

| Name | SEQ ID No | Sequence |
|---|---|---|
| 518-548 | 1 | 5'-CTGGGGGCAAAGGCTCTGCTCTCACACCCAG-3' |
| 831-864 | 2 | 5'-GGCTGAGGGGGCAGCAGGTTTGAGGCCCTCAGCC-3' |
| 832-863 | 3 | 5'-GCTGAGGGGGCAGCAGGTTTGAGGCCCTCAGC-3' |
| 834-861 | 4 | 5'-TGAGGGGGCAGCAGGTTTGAGGCCCTCA-3' |
| 1039-1073 | 5 | 5'-GCCTGGAGGATGCAGGCATTCTTACTGCTGCAGGC-3' |
| 1190-1222 | 6 | 5'-AGGCTCGTGGGGAAAGGCGGCCCAGCTCAGCCT-3' |
| 1367-1392 | 7 | 5'-GCTCTCGCTGCTGCTGCGGGGAGAGC-3' |
| 1816-1841 | 8 | 5'-ACCTGTACAAATCTGGCTCCGCAGGT-3' |
| 1821-1853 | 9 | 5'-CGGAGGTGGGCCACCTGTACAAATCTGGCTCCG-3' |
| 2121-2141 | 10 | 5'-AAGCATCAACACTCCATGCTT-3' |
| Scramble | 18 | 5'-TGTCTGGTTGCAAAGCCTGGCATAAAGACA-3' |

TABLE 2

Signal-to-noise ratios.

| SQRM | RNA | ODN | SQR |
|---|---|---|---|
| 518-548 | 2.3 +/− 0.8 | 70.6 +/− 16.0 | 2.0 +/− 0.6 |
| 831-864 | 1.8 +/− 0.2 | 33.0 +/− 4.2 | 1.3 +/− 0.2 |
| 832-863 | 1.1 +/− 0.1 | 57.6 +/− 6.6 | 1.6 +/− 0.2 |
| 834-861 | 4.4 +/− 2.4 | 150.6 +/− 61.2 | 1.9 +/− 0.8 |
| 1039-1073 | 2.2 +/− 0.5 | 39.2 +/− 8.6 | 2.7 +/− 0.6 |
| 1190-1222 | 14.5 +/− 1.6 | 57.6 +/− 5.6 | 2.2 +/− 0.4 |
| 1367-1392 | 1.1 +/− 0.3 | 51.1 +/− 13.7 | 2.0 +/− 0.4 |
| 1816-1841 | 1.2 +/− 0.3 | 17.8 +/− 3.5 | 2.5 +/− 0.5 |
| 1821-1853 | 3.2 +/− 1.2 | 63.0 +/− 7.8 | 3.3 +/− 2.3 |
| 2121-2141 | 3.8 +/− 1.9 | 207.0 +/− 22.9 | 2.9 +/− 1.0 |

Figure 2:
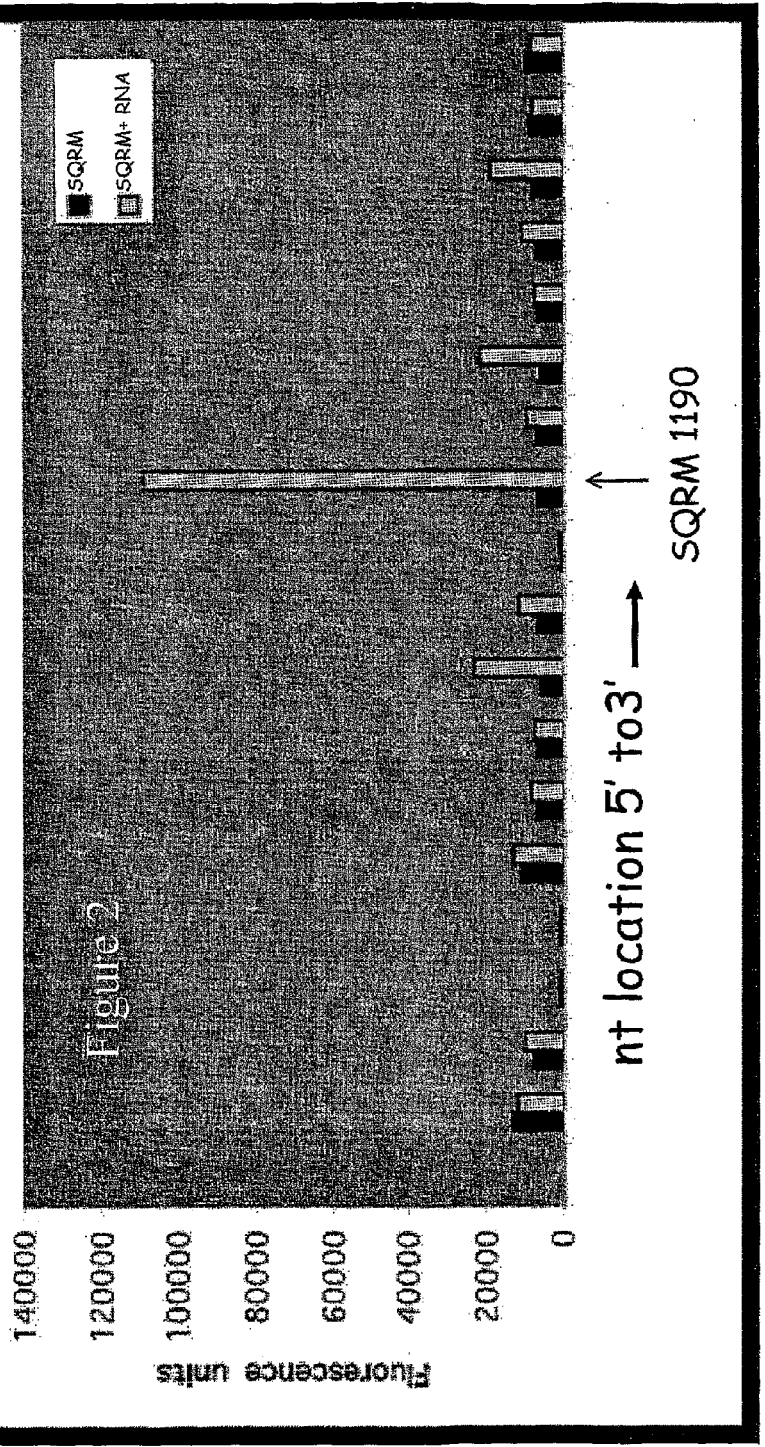
FIG. 2. Fluorescence of SQRM molecules upon incubation with bcl-6 mRNA. Six SQRMs were hybridized with in vitro-transcribed human bcl-6 targeted mRNA (2.4 kb). Of these SQRMs, 1190-1222 was shown to open, exhibiting a signal-to-noise ratio of 15:1. Light bars; SQRM alone; dark bars; SQRM+RNA.

Ten SQRMs (self-quenching reporter molecules) each were synthesized to map the full-length, 2.4 kb, bcl-6 mRNA SQRM 1190-1222 showed a favorable signal to-noise ratio (14.5 (+/−1.5):1; FIG. 2). Hybridization of SQRM 1190-1222 with the bcl-6 transcript was confirmed using an in vitro RNaseH cleaving assay. In vitro-transcribed mRNA was incubated with SQRM 1190-1222, or with two sense SQRM corresponding to non-opening locations 831-864 and 1367-1392, which yielded fragments of the expected size (1.1 and 1.3 kDa; FIG. 3A). Specificity of cutting was demonstrated by the fact that neither of the control sequences had any effect on the mRNA; bcl-6 mRNA incubated with these ODN, or with enzyme alone, remained intact.

Next, SQRM 1190-1222 was incubated with total cellular RNA derived from Louckes Burkitt's Lymphoma cells, which express the bcl-6 gene, and K562 BCR/ABL-1 (+) myeloid leukemia cells, which do not. Fluorescence was monitored using a plate reader An ODN completely complementary to the SQRM served as the arbitrary 100% fluorescence control. As expected, SQRM fluorescence increased in the Louckes cell RNA when compared with that observed in the K562 RNA. Specificity was further demonstrated by the observation that fluorescence was proportional to the amount of RNA in which the SQRM was incubated. The signal to-noise ratio for SQRM 1190-1222 when incubated in 40 mg of Louckes RNA was 2-fold higher than when incubated in 20 mg of RNA (FIG. 3B).

These findings demonstrate that bcl-6 mRNA contains regions that are available for hybridization, and that one such region is the region complementary to AGGCTCGTGGG-GAAAGGCGGCCCAGCTCAGCCT (SQRM-1190-1222; SEQ ID No: 6).

Example 2

Antisense Oligo-Deoxynucleotides Complementary to Bcl-6 RNA Decrease viability of Lymphoma Cells and their Bcl-6 Expression Materials and Experimental Methods

ODN

Antisense ODN were synthesized and purified by Integrated DNA Technologies (Coralville, Iowa). At the 3' and 5' end of each molecule were 5 phosphorothioate bonds; the intervening bonds were phosphodiester. siRNA molecules were synthesized, HPLC purified, deprotected and annealed by Dharmacon (Lafayette, Colo.).

Viability Assays

5 µg ODN or siRNA was transfected into Louckes cells using an Amaxa nucleoporator. Immediately afterwards, 1.5×

Figure 4:
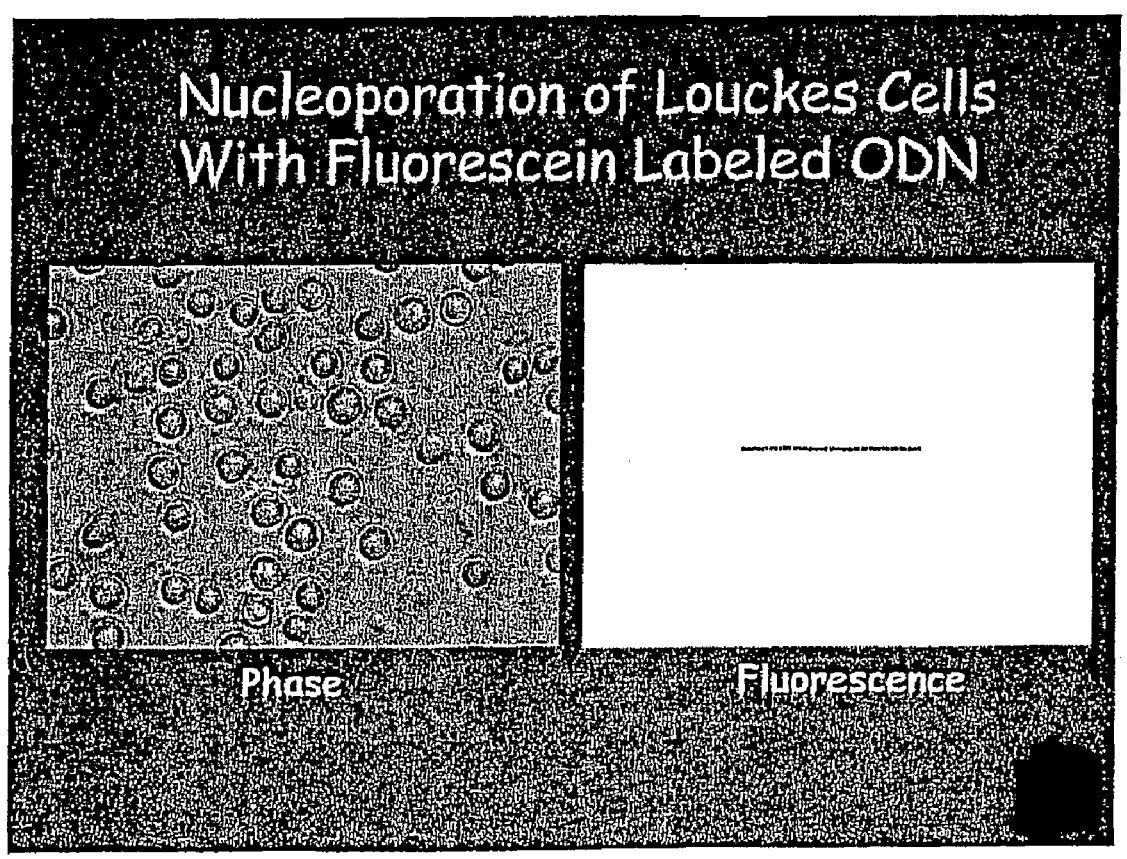
FIG. 4. Transfection efficiency of ODN or siRNA by nucleoporation. Left panel: phase contrast microscope. Right panel: Fluorescence microscope, used to detect uptake of fluorescein-labeled ODN.

1^6 cells were placed in 1.5 mL fresh media and cultured for 6 hours (ODN) or 48 hours (siRNA). Viability of cells was assessed by trypan blue exclusion. Transfection efficiency was about 95%, and cell viability was over 90% (depicted in FIG. 4).

Reverse Transcription and Real-Time PCR

Cells were washed twice in PBS and total RNA was isolated as described above. The RNA was treated with RQ-DNAse and re-purified with the Qiagen kit. The reverse transcription was performed in 20 μL total volume with 300 ng of RNA using M-MLV Reverse transcriptase (Invitrogen) and random hexamers at 10 mM concentration. Then 1 μL of cDNA was used for the real time PCR reaction. The reaction was performed in triplicates each time for bcl-6 and 18S as an internal standard. The negative control was RNA (no RT reaction). Antisense ODN and siRNA stored in nuclease-free water at −80° C. Control cells were subjected to the nucleofection procedure but in the absence of ODN.

Primers and probe for the Real Time PCR were designed with Molecular Beacon Program from BioRad and synthesized and HPLC purified by Nucleic Acid Facility of the University of Pennsylvania). The sequences were as follows:

For bcl-6: Forward primer: 5'-CCA ACC AAG CTG AGT GCC AG (SEQ ID No: 12); Reverse primer: 5'-GGT GCA TGT AGA GTG GTG AGT G (SEQ ID No: 13); probe: 5'-CTC CAC CAT CCC ACA AGC CAG CCG (SEQ ID No: 14). The probe was labeled with FAM at 5' end and Black whole 1 quencher at the 3' end.

For 18S: Forward primer: 5'-GGA CAT CTA AGG GCA TCA CAG ACC-3' (SEQ ID No: 15); Reverse primer: 5'-TGA CTC AAC ACG GGA AAC CTC AC-3' (SEQ ID No: 16); probe: 5'-TGG CTG AAC GCC ACT TGT CCC TCT AA-3' (SEQ ID No: 17). (FAM at the 5' end and TAMRA quencher at the 3' end)-hybridizes between 1294 and 1614 to human 18S.

The protocol for PCR reaction consisted of: 50° C. for 2 min, and denaturation at 95° C. for 10 min, followed by 36 cycles of 15 sec denaturation at 92° C. and 1 min of annealing and elongation at 60° C. The expected 133 bp bcl-6 PCR product was resolved on 1% agarose gel to confirm the specificity of the reaction.

Western Blot

Cells incubated for the appropriate time with nucleic acid molecules were washed and lysed in triple lysis buffer to obtain a total (nuclear and cytoplasmic) protein cell extract. In each case equal amount (100 μg) of the total protein was resolved on 10% polyacrylamide gel and transferred to the PVDF membrane and then probed with the primary antibody against bcl-6 (rabbit polyclonal, C-19, Santa Cruz Biotechnology) at 1:500 dilution from at 4° C. overnight. After 3 washes in TBS-T buffer the secondary antibody (anti-rabbit, HRP conjugated; 1:1000 dilution) was incubated with the membrane for 1 hour at room temperature. The visualization was performed with ECL (+) reagent. The same PVDF membrane was then stripped with stripping buffer and probed with antibody against beta actin (1:3000 dilution).

Results

Figure 5:
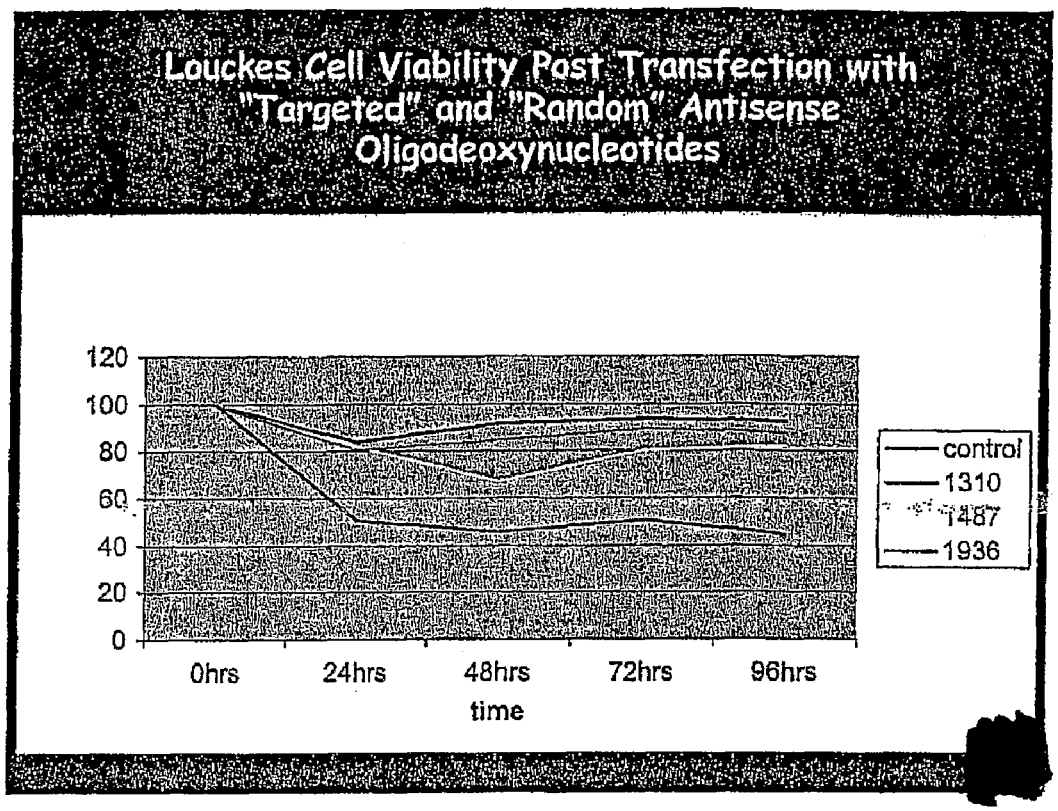
FIG. 5. Effect of bcl-6-derived ODN on the viability of bcl-6-expressing lymphoma cells.
Figure 6:
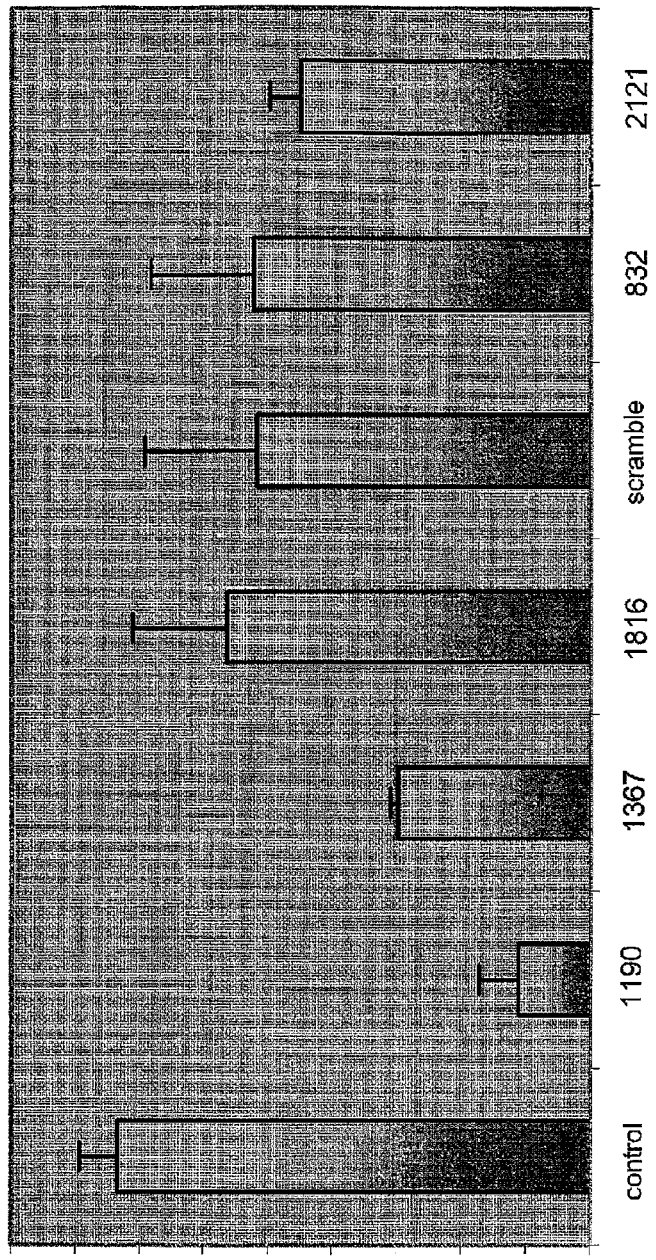
FIG. 6. Effect of bcl-6-derived ODN on bcl-6 mRNA expression in lymphoma cells.
Figure 7:
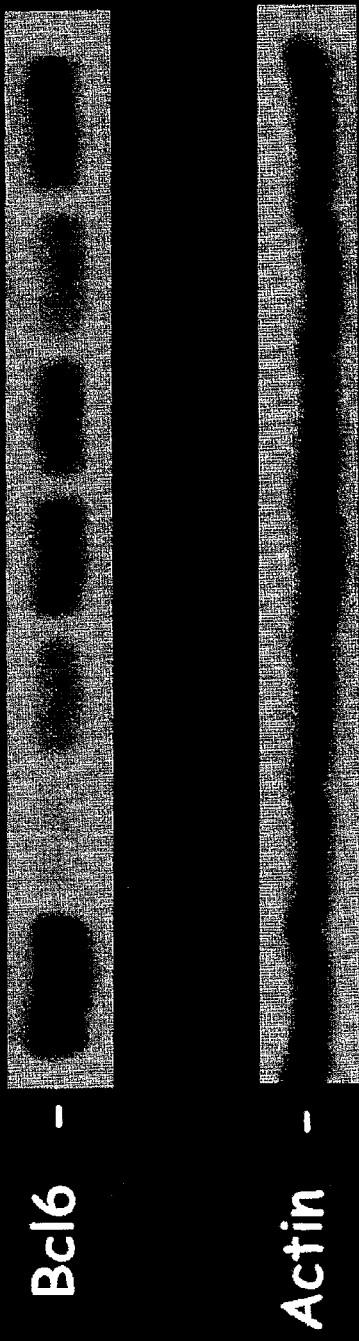
FIG. 7. Effect of bcl-6-derived ODN on bcl-6 protein expression in lymphoma cells. Lanes from left to righ: positive control ODN; SQRM 1190-1222; SQRM 1367; SQRM 1816; scrambled; SQRM 831-864; SQRM 2121-2141.

Next, antisense oligo-deoxynucleotides (ODN) corresponding to the sequences of the SQRM were transfected into bcl-6 expressing Louckes (Burkitt's lymphoma) cells and cell viability was determined for four consecutive days. Cells transfected with SQRM-1190-1222 exhibited a 50% drop in viability within 24 hours (FIG. 5). A smaller, but persistent effect on viability was seen with SQRM-1367-1392. SQRM-1190-1222 and SQRM-1367-1392 also caused 7-fold and 2.5-fold decreases in bcl-6 mRNA expression, respectively (FIG. 6). A smaller but significant decrease in bcl-6 mRNA expression was observed with SQRM-2121-2141. The effects on bcl-6 mRNA expression were confirmed by Western blot, which demonstrated an 80% decrease of bcl-6 proteins levels upon incubation with SQRM-1190-1222 (FIG. 7).

These findings show that bcl-6 mRNA expression can be reduced by introduction of antisense ODN complementary to the bcl-6 sequence. The findings further show that introduction of the antisense ODN can reduce the viability of bcl-6-expressing lymphoma cells.

Example 3

Figure 8:
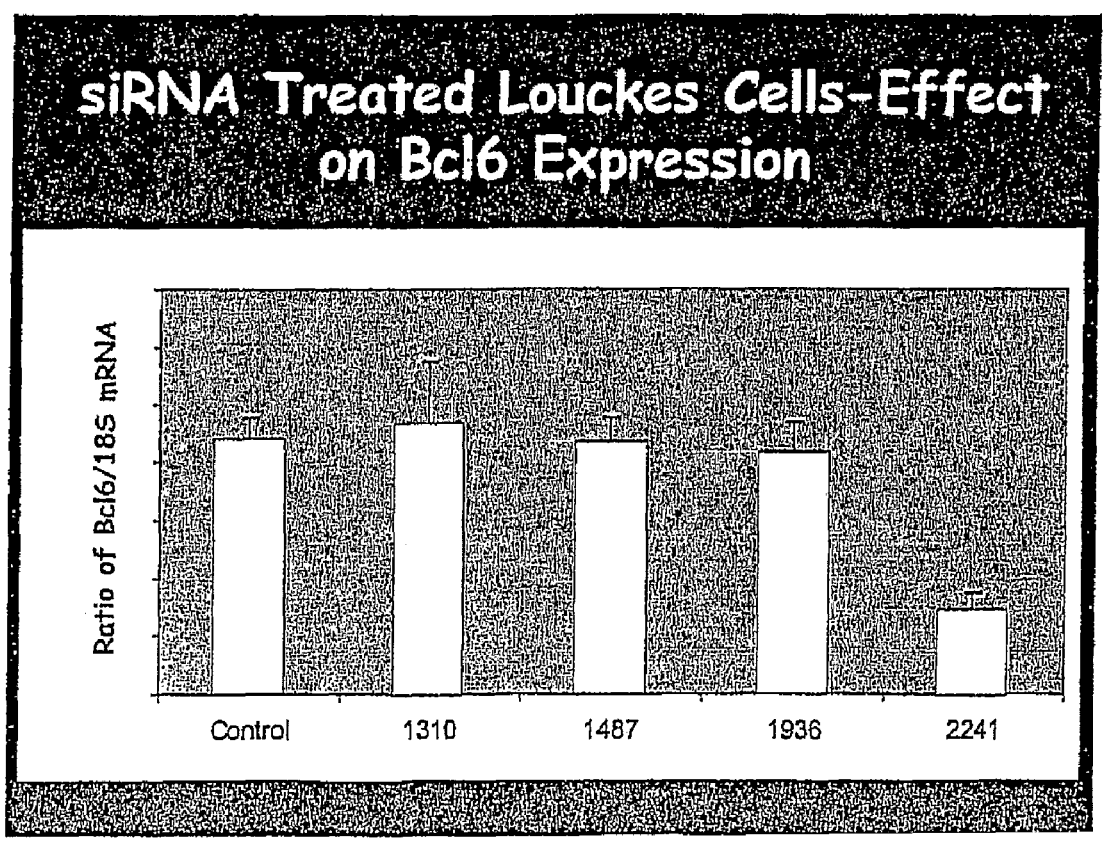
FIG. 8. Effect of bcl-6-derived siRNA on bcl-6 mRNA expression in lymphoma cells.
Figure 9:
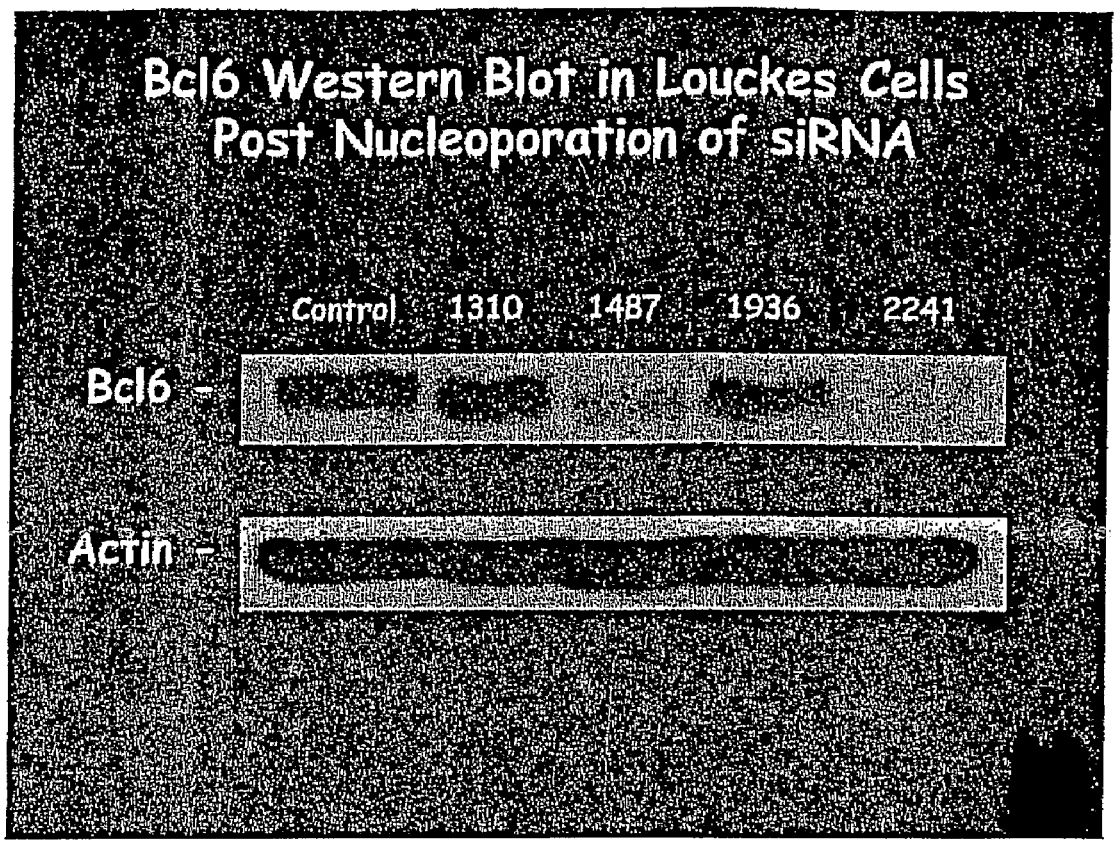
FIG. 9. Effect of bcl-6-derived siRNA on bcl-6 protein expression in lymphoma cells.

Short Interfering RNA Molecules Corresponding to Bcl-6 RNA Sequence Decrease Viability of Lymphoma Cells and their Bcl-6 Expression Next, small interfering RNA molecules (siRNA) corresponding to segments of bcl-6 RNA sequence were synthesized and incubated with Louckes cells, and bcl-6 expression assayed by Western blot. siRNA corresponding to SQRM-1190-1222 reduced bcl-6 mRNA expression by three-fold, in a dose-dependent manner (FIG. 8). These findings were confirmed by Western blot, which revealed an effect of siRNA corresponding to both SQRM-2121 and SQRM-1367 on bcl-6 protein expression (FIG. 9).

These findings demonstrate that siRNA corresponding to segments of bcl-6 RNA sequence can reduce bcl-6 mRNA and protein expression in bcl-6-expressing lymphoma cells.

Example 4

Figure 10:
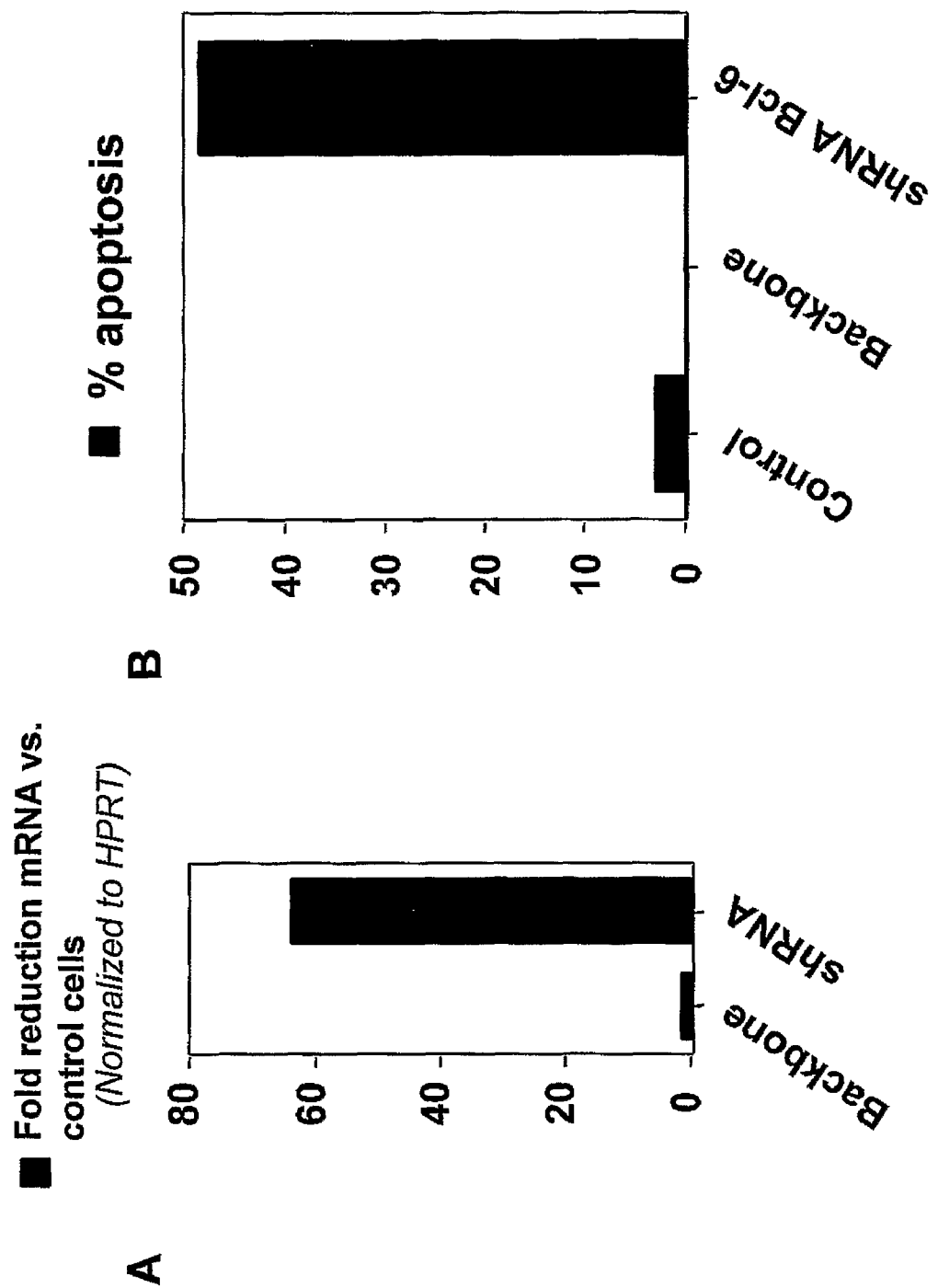
FIG. 10. shRNA reduction of Bcl-6 and induction of apoptosis in diffuse large B-cell lymphoma (DLBCL) cells. A: Fold reduction of Bcl-6 mRNA in GFP-virus vs. shRNA-GFP-virus-infected Ly7 cells compared to control cells. Values are normalized to HPRT as an internal standard mRNA. B: percent of Ly7 cells undergoing apoptosis after 48 hours post-infection. Depicted are control cells, and cells infected with GFP-virus and shRNA-GFP-virus cells.

Lentiviruses Expressing Short Hairpin Sequences Complementary to Bcl mRNA Decrease Viability of Lymphoma Cells and their Bcl-6 Expression Region 2121 was converted to a short hairpin RNA (shRNA) sequence suitable for expression in a GFP/lentiviral vector. The shRNA sequence was subcloned into a GFP/lentiviral vector and used to transfect Ly7 DLBCL cells and bcl-6 mRNA levels in GFP-positive cells assessed. shRNA expressing lentivirus decreased bcl-6 mRNA levels 60-fold, whereas wild-type lentivirus had no measurable effect (FIG. 10A). The shRNA expressing lentivirus, but not the wild-type virus, induced apoptosis in 50% of the Ly7 cells, as detected by ethidium bromide/acridine orange staining (FIG. 10B).

The findings of this Example demonstrate that expression of shRNA derived from accessible regions of bcl-6 mRNA decreases bcl-6 expression and induces apoptosis in lymphoma cells.

Example 5

Identification of Additional siRNA Sequences Corresponding to Accessible Regions of Bcl-6 mRNA 21-nucleotide (nt) fragments of the accessible regions of bcl-6 depicted in Table 1 are synthesized and tested for their ability to reduce bcl-6 mRNA expression and reduce viability of lymphoma cells, by the methods of previous Examples. Several sequences that are found to be effective by transfection are subcloned into a lentiviral vector and added to lymphoma cells in culture. Lentiviral and other vectors expressing the effective sequences and other reagents comprising the effective sequences are administered to lymphoma patients, and are found to induce apoptosis in the lymphoma cells.

Example 6

Derivation of Additional shRNA Sequences Corresponding to Accessible Regions of Bcl-6 mRNA ShRNA sequences corresponding to accessible regions of bcl-6 mRNA are derived using algorithms known in the art. Typical siRNA sequences have the following characteristics:

1). Begins with a purine (G or A) residue; 2). Contains 5 bases for the restriction site overhang at the 5' end, followed by 19-23 bases of sense strand, 8-9 bases of hairpin loop, 19-23 bases of antisense strand, 6 bases of a unique restriction site, and 1-2 bases for pairing with the restriction site overhang on the complementary strand.

The 19-23 nucleotide sequence should have the following characteristics: 1). Is preferably 19 nucleotides in length. 2). Is not located within the 5' and 3' untranslated regions (UTRs) nor regions near the start codon (within 75 bases). 3). Does not contain a consecutive run of 3 or more thymidine residues. 4). Has a GC content of between 40% and 60%, preferably approximately 45%. 5) Preferably has at least 3 A or T residues in positions 15-19 of the sense sequence. 6). Does not exhibit secondary structure. 7). Is specific for the gene of interest.

Several candidate shRNA sequences are subcloned into a lentiviral expression vector, then tested for activity against lymphoma cells as described in the previous Example. shRNA-lentiviruses that kill lymphoma cells are administered to lymphoma patients, and are shown to have cancer chemotherapeutic activity.

What is claimed is:

1. A method of inducing apoptosis in a bcl-6-expressing cell, comprising contacting said bcl-6-expressing cell with a composition that reduces an amount of said bcl-6 protein or of a ribonucleic acid molecule encoding said bcl-6 protein, thereby inducing apoptosis in a bcl-6-expressing cell, wherein said composition comprises a nucleic acid molecule complementary to the sequence set forth in SEQ ID NO: 6.

2. The method of claim 1, wherein said cell is a lymphoma cell.

3. The method of claim 2, wherein said lymphoma cell is a non-Hodgkin's lymphoma cell.

4. A method of treating a subject with a lymphoma comprising a bcl-6-expressing lymphoma cell, comprising contacting said subject with a composition that reduces an amount of said bcl-6 protein or of a ribonucleic acid molecule encoding said bcl-6 protein, thereby treating said subject with said lymphoma, wherein said composition comprises a nucleic acid molecule complementary to the sequence set forth in SEQ ID NO: 6.

5. The method of claim 4, wherein said lymphoma is a non-Hodgkin's lymphoma.

6. A method of inducing apoptosis in a bcl-6-expressing cell, comprising contacting said bcl-6-expressing cell with a composition comprising a nucleic acid molecule complementary to the sequence set forth in SEQ ID NO: 6, thereby inducing apoptosis in a bcl-6-expressing cell.

7. The method of claim 6, wherein said cell is a lymphoma cell.

8. The method of claim 7, wherein said lymphoma cell is a non-Hodgkin's lymphoma cell.

9. The method of claim 6, wherein said nucleic acid molecule is an oligo-deoxyribonucleic acid (ODN) molecule.

10. A method of treating a subject with a lymphoma comprising a bcl-6-expressing lymphoma cell, comprising contacting said subject with a composition comprising a nucleic acid molecule complementary to the sequence set forth in SEQ ID NO: 6, thereby treating said subject with said lymphoma.

11. The method of claim 10, wherein said lymphoma is a non-Hodgkin's lymphoma.

12. The method of claim 10, wherein said nucleic acid molecule is an oligo-deoxyribonucleic acid (ODN) molecule.

13. A method of inducing apoptosis in a bcl-6-expressing cell, comprising contacting said bcl-6-expressing cell with a composition comprising a nucleic acid molecule corresponding to the sequence set forth in SEQ ID NO: 6, thereby inducing apoptosis in a bcl-6-expressing cell.

14. The method of claim 13, wherein said cell is a lymphoma cell.

15. The method of claim 14, wherein said lymphoma cell is a non-Hodgkin's lymphoma cell.

16. The method of claim 13, wherein said nucleic acid molecule is a short interfering ribonucleic acid (siRNA) molecule.

17. The method of claim 13, wherein said nucleic acid molecule is a short hairpin RNA (shRNA) molecule.

18. A method of treating a subject with a lymphoma comprising a bcl-6-expressing lymphoma cell, said method comprising contacting said subject with a composition comprising a nucleic acid molecule corresponding to the sequence set forth in SEQ ID NO: 6, thereby treating said subject with said lymphoma.

19. The method of claim 18, wherein said lymphoma is a non-Hodgkin's lymphoma.

20. The method of claim 18, wherein said nucleic acid molecule is a short interfering ribonucleic acid (siRNA) molecule.

21. The method of claim 18, wherein said nucleic acid molecule is a short hairpin RNA (shRNA) molecule.

22. A method of inducing apoptosis in a bcl-6-expressing cell, comprising contacting said bcl-6-expressing cell with a vector expressing a nucleic acid molecule complementary to the sequence set forth in SEQ ID NO: 6, thereby inducing apoptosis in said bcl-6-expressing cell.

23. The method of claim 22, wherein said cell is a lymphoma cell.

24. The method of claim 23, wherein said lymphoma cell is a non-Hodgkin's lymphoma cell.

25. The method of claim 22, wherein said vector is a lentiviral vector.

26. The method of claim 22, wherein said nucleic acid molecule is an oligo-deoxyribonucleic acid (ODN) molecule.

27. A method of treating a subject with a lymphoma comprising a bcl-6-expressing lymphoma cell, comprising contacting said subject with a vector expressing a nucleic acid molecule complementary to the sequence set forth in SEQ ID NO: 6, thereby treating said subject with said lymphoma.

28. The method of claim 27, wherein said lymphoma is a non-Hodgkin's lymphoma.

29. The method of claim 27, wherein said vector is a lentiviral vector.

30. The method of claim 27, wherein said nucleic acid molecule is an oligo-deoxyribonucleic acid (ODN) molecule.

31. A method of inducing apoptosis in a bcl-6-expressing cell, comprising contacting said bcl-6-expressing cell with a vector expressing a nucleic acid molecule corresponding to the sequence set forth in SEQ ID NO: 6, thereby inducing apoptosis in said bcl-6-expressing cell.

32. The method of claim 31, wherein said cell is a lymphoma cell.

33. The method of claim 32, wherein said lymphoma cell is a non-Hodgkin's lymphoma cell.

34. The method of claim 31, wherein said vector is a lentiviral vector.

35. The method of claim 31, wherein said nucleic acid molecule is a short interfering ribonucleic acid (siRNA) molecule.

36. The method of claim 31, wherein said nucleic acid molecule is a short hairpin RNA (shRNA) molecule.

37. A method of treating a subject with a lymphoma comprising a bcl-6-expressing lymphoma cell, comprising contacting said subject with a vector expressing a nucleic acid molecule corresponding to the sequence set forth in SEQ ID NO: 6, thereby treating said subject with said lymphoma.

38. The method of claim 37, wherein said lymphoma is a non-Hodgkin's lymphoma.

39. The method of claim 37, wherein said vector is a lentiviral vector.

40. The method of claim 37, wherein said nucleic acid molecule is a short interfering ribonucleic acid (siRNA) molecule.

41. The method of claim 37, wherein said nucleic acid molecule is a short hairpin RNA (shRNA) molecule.

42. The method of claim 6, wherein said contacting reduces the amount of the bcl-6 protein expressed by said bcl-6-expressing cell or of a ribonucleic acid (RNA) molecule encoding said bcl-6 protein.

43. The method of claim 10, wherein said contacting reduces the amount of the bcl-6 protein expressed by said bcl-6-expressing cell or of a ribonucleic acid (RNA) molecule encoding said bcl-6 protein.

44. The method of claim 13, wherein said contacting reduces the amount of the bcl-6 protein expressed by said bcl-6-expressing cell or of a ribonucleic acid (RNA) molecule encoding said bcl-6 protein.

45. The method of claim 18, wherein said contacting reduces the amount of the bcl-6 protein expressed by said bcl-6-expressing cell or of a ribonucleic acid (RNA) molecule encoding said bcl-6 protein.

46. The method of claim 22, wherein said contacting reduces the amount of the bcl-6 protein expressed by said bcl-6-expressing cell or of a ribonucleic acid (RNA) molecule encoding said bcl-6 protein.

47. The method of claim 27, wherein said contacting reduces the amount of the bcl-6 protein expressed by said bcl-6-expressing cell or of a ribonucleic acid (RNA) molecule encoding said bcl-6 protein.

48. The method of claim 31, wherein said contacting reduces the amount of the bcl-6 protein expressed by said bcl-6-expressing cell or of a ribonucleic acid (RNA) molecule encoding said bcl-6 protein.

49. The method of claim 37, wherein said contacting reduces the amount of the bcl-6 protein expressed by said bcl-6-expressing cell or of a ribonucleic acid (RNA) molecule encoding said bcl-6 protein.

\* \* \* \* \*

SEQUENCE LISTING

<160> NUMBER OF SEQ ID NOS: 18

<210> SEQ ID NO 1
<211> LENGTH: 31
<212> TYPE: DNA
<213> ORGANISM: Artificial
<220> FEATURE:
<223> OTHER INFORMATION: Probe

<400> SEQUENCE: 1
ctgggggcaa aggctctgct ctcacaccca g                          31

<210> SEQ ID NO 2
<211> LENGTH: 34
<212> TYPE: DNA
<213> ORGANISM: Artificial
<220> FEATURE:
<223> OTHER INFORMATION: Probe

<400> SEQUENCE: 2
ggctgagggg gcagcaggtt tgaggccctc agcc                       34

<210> SEQ ID NO 3
<211> LENGTH: 32
<212> TYPE: DNA
<213> ORGANISM: Artificial
<220> FEATURE:
<223> OTHER INFORMATION: Probe

<400> SEQUENCE: 3
gctgaggggg cagcaggttt gaggccctca gc                         32

<210> SEQ ID NO 4
<211> LENGTH: 32
<212> TYPE: DNA
<213> ORGANISM: Artificial
<220> FEATURE:
<223> OTHER INFORMATION: Probe

<400> SEQUENCE: 4
gctgaggggg cagcaggttt gaggccctca gc                         32

<210> SEQ ID NO 5
<211> LENGTH: 35

```
<212> TYPE: DNA
<213> ORGANISM: Artificial
<220> FEATURE:
<223> OTHER INFORMATION: Probe

<400> SEQUENCE: 5
gcctggagga tgcaggcatt cttactgctg caggc                           35

<210> SEQ ID NO 6
<211> LENGTH: 33
<212> TYPE: DNA
<213> ORGANISM: Artificial
<220> FEATURE:
<223> OTHER INFORMATION: Probe

<400> SEQUENCE: 6
aggctcgtgg ggaaaggcgg cccagctcag cct                             33

<210> SEQ ID NO 7
<211> LENGTH: 26
<212> TYPE: DNA
<213> ORGANISM: Artificial
<220> FEATURE:
<223> OTHER INFORMATION: Probe

<400> SEQUENCE: 7
gctctcgctg ctgctgcggg gagagc                                     26

<210> SEQ ID NO 8
<211> LENGTH: 26
<212> TYPE: DNA
<213> ORGANISM: Artificial
<220> FEATURE:
<223> OTHER INFORMATION: Probe

<400> SEQUENCE: 8
acctgtacaa atctggctcc gcaggt                                     26

<210> SEQ ID NO 9
<211> LENGTH: 33
<212> TYPE: DNA
<213> ORGANISM: Artificial
<220> FEATURE:
<223> OTHER INFORMATION: Probe

<400> SEQUENCE: 9
cggaggtggg ccacctgtac aaatctggct ccg                             33

<210> SEQ ID NO 10
<211> LENGTH: 21
<212> TYPE: DNA
<213> ORGANISM: Artificial
<220> FEATURE:
<223> OTHER INFORMATION: Probe

<400> SEQUENCE: 10
aagcatcaac actccatgct t                                          21

<210> SEQ ID NO 11
<211> LENGTH: 3536
<212> TYPE: DNA
<213> ORGANISM: Homo sapiens

<400> SEQUENCE: 11
ggcccctcga gcctcgaacc ggaacctcca aatccgagac gctctgctta tgaggacctc    60
```

-continued

| | |
|---|---|
| gaaatatgcc ggccagtgaa aaaatcttat ggctttgagg gcttttggtt ggccaggggc | 120 |
| agtaaaaatc tcggagagct gacaccaagt cctcccctgc cacgtagcag tggtaaagtc | 180 |
| cgaagctcaa attccgagaa ttgagctctg ttgattctta gaactggggt tcttagaagt | 240 |
| ggtgatgcaa gaagtttcta ggaaaggccg gacaccaggt tttgagcaaa attttggact | 300 |
| gtgaagcaag gcattggtga agacaaaatg gcctcgccgg ctgacagctg tatccagttc | 360 |
| acccgccatg ccagtgatgt tcttctcaac cttaatcgtc tccggagtcg agacatcttg | 420 |
| actgatgttg tcattgttgt gagccgtgag cagtttagag cccataaaac ggtcctcatg | 480 |
| gcctgcagtg gcctgttcta tagcatcttt acagaccagt tgaaatgcaa ccttagtgtg | 540 |
| atcaatctag atcctgagat caaccctgag ggattctgca tcctcctgga cttcatgtac | 600 |
| acatctcggc tcaatttgcg ggagggcaac atcatggctg tgatggccac ggctatgtac | 660 |
| ctgcagatgg agcatgttgt ggacacttgc cggaagttta ttaaggccag tgaagcagag | 720 |
| atggtttctg ccatcaagcc tcctcgtgaa gagttcctca acagccggat gctgatgccc | 780 |
| caagacatca tggcctatcg gggtcgtgag gtggtggaga caacctgcc actgaggagc | 840 |
| gcccctgggt gtgagagcag agcctttgcc cccagcctgt acagtggcct gtccacaccg | 900 |
| ccagcctctt attccatgta cagccacctc cctgtcagca gcctcctctt ctccgatgag | 960 |
| gagtttcggg atgtccggat gctgtggcc aaccccttcc ccaaggagcg ggcactccca | 1020 |
| tgtgatagtg ccaggccagt ccctggtgag tacagccggc cgactttgga ggtgtccccc | 1080 |
| aatgtgtgcc acagcaatat ctattcaccc aaggaaacaa tcccagaaga ggcacgaagt | 1140 |
| gatatgcact acagtgtggc tgagggcctc aaacctgctg ccccctcagc ccgaaatgcc | 1200 |
| ccctacttcc cttgtgacaa ggccagcaaa gaagaagaga gaccctcctc ggaagatgag | 1260 |
| attgccctgc atttcgagcc ccccaatgca cccctgaacc ggaagggtct ggttagtcca | 1320 |
| cagagccccc agaaatctga ctgccagccc aactcgccca cagaggcctg cagcagtaag | 1380 |
| aatgcctgca tcctccaggc ttctggctcc cctccagcca agagccccac tgaccccaaa | 1440 |
| gcctgcaact ggaagaaata caagttcatc gtgctcaaca gcctcaacca gaatgccaaa | 1500 |
| ccaggggggc ctgagcaggc tgagctgggc cgccttttccc cacgagccta cacggcccca | 1560 |
| cctgcctgcc agccacccat ggagcctgag aaccttgacc tccagtcccc aaccaagctg | 1620 |
| agtgccagcg gggaggactc caccatccca caagccagcc ggctcaataa catcgttaac | 1680 |
| aggtccatga cgggctctcc ccgcagcagc agcgagagcc actcaccact ctacatgcac | 1740 |
| cccccgaagt gcacgtcctg cggctctcag tccccacagc atgcagagat gtgcctccac | 1800 |
| accgctggcc ccacgttcgc tgaggagatg ggagagaccc agtctgagta ctcagattct | 1860 |
| agctgtgaga acggggcctt cttctgcaat gagtgtgact gccgcttctc tgaggaggcc | 1920 |
| tcactcaaga ggcacacgct gcagacccac agtgacaaac cctacaagtg tgaccgctgc | 1980 |
| caggcctcct tccgctacaa gggcaacctc gccagccaca gaccgtcca taccggtgag | 2040 |
| aaaccctatc gttgcaacat ctgtgggcc cagttcaacc ggccagccaa cctgaaaacc | 2100 |
| cacactcgaa ttcactctgg agagaagccc tacaaatgcg aaacctgcgg agccagattt | 2160 |
| gtacaggtgg cccacctccg tgcccatgtg cttatccaca ctggtgagaa gccctatccc | 2220 |
| tgtgaaatct gtggcacccg tttccggcac cttcagactc tgaagagcca cctgcgaatc | 2280 |
| cacacaggag agaaaacctta ccattgtgag aagtgtaacc tgcatttccg tcacaaaagc | 2340 |
| cagctcgcgac ttcacttgcg ccagaagcat ggcgccatca ccaacaccaa ggtgcaatac | 2400 |
| cgcgtgtcag ccactgacct gcctccggag ctccccaaag cctgctgaag catggagtgt | 2460 |

-continued

```
tgatgctttc gtctccagcc ccttctcaga atctacccaa aggatactgt aacactttac    2520
aatgttcatc ccatgatgta gtgcctcttt catccactag tgcaaatcat agctgggggt    2580
tgggggtggt gggggtcggg gcctggggga ctggagccg cagcagctcc cctcccccca     2640
ctgccataaa acattaagaa aatcatattg cttcttctcc tatgtgtaag gtgaaccatg    2700
tcagcaaaaa gcaaaatcat tttatatgtc aaagcagggg agtatgcaaa agttctgact    2760
tgactttagt ctgcaaaatg aggaatgtat atgttttgtg ggaacagatg tttcttttgt    2820
atgtaaatgt gcattctttt aaaagacaag acttcagtat gttgtcaaag agagggcttt    2880
aattttttta accaaaggtg aaggaatata tggcagagtt gtaaatatat aaatatatat    2940
atatataaaa taaatatata taaacctaac aaagatatat taaaaatata aaactgcgtt    3000
aaaggctcga ttttgtatct gcaggcagac acggatctga aatctttat tgagaaagag     3060 cacttaagag aatattttaa gtattgcatc tgtataagta agaaaatatt ttgtctaaaa    3120
tgcctcagtg tatttgtatt ttttgcaag tgaaggttta caatttacaa agtgtgtatt     3180
aaaaaaaacc caagaaccc aaaaatctgc agaaggaaaa atgtgtaatt ttgttctagt     3240
tttcagtttg tatatacccg tacaacgtgt cctcacggtg cctttttca cggaagtttt     3300 caatgatggg cgagcgtgca ccatcccttt ttgaagtgta ggcagacaca gggacttgaa    3360
gttgttacta actaaactct ctttgggaat gtttgtctca tcccattctg cgtcatgctt    3420
gtgtgataac tactccggag acagggtttg gctgtgtcta aactgcatta ccgcgttgta    3480
aaaaatagct gtaccaatat aagaataaaa tgttggaaag tcgcaaaaaa aaaaaa       3536
```

<210> SEQ ID NO 12
<211> LENGTH: 20
<212> TYPE: DNA
<213> ORGANISM: Artificial
<220> FEATURE:
<223> OTHER INFORMATION: Primer

<400> SEQUENCE: 12
ccaaccaagc tgagtgccag                                                  20

<210> SEQ ID NO 13
<211> LENGTH: 22
<212> TYPE: DNA
<213> ORGANISM: Artificial
<220> FEATURE:
<223> OTHER INFORMATION: Primer

<400> SEQUENCE: 13
ggtgcatgta gagtggtgag tg                                               22

<210> SEQ ID NO 14
<211> LENGTH: 24
<212> TYPE: DNA
<213> ORGANISM: Artificial
<220> FEATURE:
<223> OTHER INFORMATION: Probe

<400> SEQUENCE: 14
ctccaccatc ccacaagcca gccg                                             24

<210> SEQ ID NO 15
<211> LENGTH: 24
<212> TYPE: DNA
<213> ORGANISM: Artificial
<220> FEATURE:

```
<223> OTHER INFORMATION: Primer

<400> SEQUENCE: 15
ggacatctaa gggcatcaca gacc                                              24

<210> SEQ ID NO 16
<211> LENGTH: 23
<212> TYPE: DNA
<213> ORGANISM: Artificial
<220> FEATURE:
<223> OTHER INFORMATION: Primer

<400> SEQUENCE: 16
tgactcaaca cgggaaacct cac                                               23

<210> SEQ ID NO 17
<211> LENGTH: 26
<212> TYPE: DNA
<213> ORGANISM: Artificial
<220> FEATURE:
<223> OTHER INFORMATION: Probe

<400> SEQUENCE: 17
tggctgaacg ccacttgtcc ctctaa                                            26

<210> SEQ ID NO 18
<211> LENGTH: 30
<212> TYPE: DNA
<213> ORGANISM: Artificial
<220> FEATURE:
<223> OTHER INFORMATION: Probe

<400> SEQUENCE: 18
tgtctggttg caaagcctgg cataaagaca                                        30
```